(12) United States Patent
Wain-Hobson et al.

(10) Patent No.: US 8,541,206 B2
(45) Date of Patent: Sep. 24, 2013

(54) DIFFERENTIAL AMPLIFICATION OF MUTANT NUCLEIC ACIDS BY PCR IN A MIXTURE OF NUCLEIC ACIDS

(75) Inventors: Simon Wain-Hobson, Montigny le Bretonneux (FR); Jean-Pierre Vartanian, Paris (FR)

(73) Assignee: Institut Pasteur, Paris (FR)

( * ) Notice: Subject to any disclaimer, the term of this patent is extended or adjusted under 35 U.S.C. 154(b) by 600 days.

(21) Appl. No.: 12/086,897

(22) PCT Filed: Dec. 28, 2006

(86) PCT No.: PCT/IB2006/004187
§ 371 (c)(1),
(2), (4) Date: Sep. 13, 2010

(87) PCT Pub. No.: WO2007/091125
PCT Pub. Date: Aug. 16, 2007

(65) Prior Publication Data
US 2011/0003282 A1    Jan. 6, 2011

(51) Int. Cl.
*C12P 19/34*    (2006.01)
(52) U.S. Cl.
USPC ........................................................ 435/91.2
(58) Field of Classification Search
None
See application file for complete search history.

(56) References Cited

U.S. PATENT DOCUMENTS 5,461,143 A  *  10/1995  Wong et al. .................. 536/17.5

OTHER PUBLICATIONS

Suspene I (Journal of General Virology, 2005, vol. 86, p. 125-129).*
Auer et al. (Nucleic Acids Research, 1996, vol. 24, No. 24, p. 5021-5025).*
Pathak et al. (PNAS, 1990, 87(16), p. 6019-6023).*
Israeli et al. (Cancer Research, 1994, 54:6306-6310).*
Kramer MF and Coen DM (Current Protocols in Molecular Biology, 2001, 15.1.1-15.1.14.*
Wong et al. (Journal of Virology, 1989, p. 5464-5468).*
Rodolph Suspéne, et al., "Recovery of APOBEC3-edited human immunodeficiency virus G→A hypermutants by differential DNA denaturation PCR," Journal of General Virology (2005), 86:125-129.
Alekos Athanasiadis, et al., "Widespread A-to-I RNA Editing of Alu-Containing mRNAs in the Human Transcriptome," PLos Biology (Dec. 2004), vol. 2, Issue 12.

* cited by examiner

*Primary Examiner* — Stephanie K Mummert
(74) *Attorney, Agent, or Firm* — Finnegan, Henderson, Farabow, Garrett & Dunner LLP

(57) ABSTRACT

A method for enriching a mutant nucleic acid in a mixture of nucleic acids, wherein the method comprises: (a) providing a nucleic acid mixture comprising a parental nucleic acid and a mutant nucleic acid of the parental nucleic acid; and (b) amplifying the nucleic acids in the nucleic acid mixture by polymerase chain reaction (PCR); wherein the mutant nucleic acid is a G→A mutant of the parental nucleic acid, which pairs with a fully complementary nucleic acid sequence to form an AT-rich nucleic acid variant of the parental nucleic acid; and wherein the AT-rich nucleic acid variant is denatured and selectively amplified by carrying out PCR using a denaturation temperature 1-3° C. lower than the lowest denaturation temperature ($T_p$) that allows amplification of the parental nucleic acid to thereby enrich the mutant nucleic acid in the nucleic acid mixture.

55 Claims, 22 Drawing Sheets

```
Ref  TGCACTGATTTGAAGAATGATACTAATACCAATAGTAGTAGCGGGAGAATGATAATGGAGAAAGGAGAGA-TAAAAAACTGCTCTTTCAATATCA
01   .....................................................A......A..........-...............
02   .....................................................A......A..........-...............
03   ....T...............................A..A..A.........A......A..........-...............
04   .....A....A...A...A.................................A......A....AA.A...AA.A.A.A........
05   .....A....A...A...A.................................A......A....AATA...AA.A.A.A........
06   .....A....A...A...A.................................A......A....AA.A...AA.A---.........
07   .....A....A...A...A.................................A......A....AA.A...AA.A---.........
08   .....A....A...A...A.................................A......A....AA.A...AA.A.A--........
09   .....A....A...A...A.................................A......A....AA.A...AA.A.A.-........
10   .....A....A...A...A.................................A......A....AA.A...AA.A.A.--.......
11   .....A....A...A...A.................................A......A....AA.A...AA.A.A.-........
12   .....A....A...A...A.................................A......A....AA.A...AA.A---.........
13   .....A....A...A...A.................................A......A....AA.A...AA.A-A--........
14   .....A....A...A...A.................................A......A....AA.A...AA.A---.........
15   .....A....A...A...A.................................A......A....AA.A...AA.A.A--........
16   .....A....A...A...A.................................A......A....AA.A...AA.A.A--........
17   .....A....A...A...A.................................A......A....AA.A...AA.A.A.-........

Ref  GCACAAGCATAAGAGATAAGGTGCAGAAAGAATATGCATTCTTTTATAAACTTGATATAGTACCAATAGATAATACCAGCTATAGGTTGATAAGT
01   .......................................................................................A.....
02   .......................................................................................A.....
03   ...............................................A.......................................A.....
04   .............................A....................A......................A.............A.....
05   .............................A....................A......................A.............A.....
06   .............................A....................A......................A......G......A.....
07   .............................A....................A......................A.............A.....
08   .............................A....................A......................A.............A.....
09   .............................A....................A......................A.............A.....
10   .............................A....................A......................A.............A.....
11   .............................A....................A......................A.............A.....
12   .............................A..........G.........A......................A...................
13   .............................A....................A...........................................
14   .............................A.................................................................
15   .............................A.................................................................
16   .................................................................................................
17   .................................................................................................
```

FIG. 2

```
Ref  GTGAAACGGTGGGGGCGGCAACGTCTAGAGACGCTCTCCCAAACACTGAAGCCAGTGGACCAGCACACTCCAAGGAAATTCCGGCACTCACCGCAGTGGAAACTGGGGC
01   A....................A................................T.......................................................
02   .....................A..........................................................A.............................
03   .....................A.........................................................................................
04   .......A........................................................................................................
05   ..........................A..........................A........................................................
06   .............T..................................................................T..............................
07   .............T....................................A...........................................T...............
08   .................................................T..............AT............................................
09   ................................................T.............................................T..............
10   ...............................................................................................A.............T
11   ..........................................................T..................................A...............
12   .............................................................................................TC................
13   ................................................................................T...............................
```

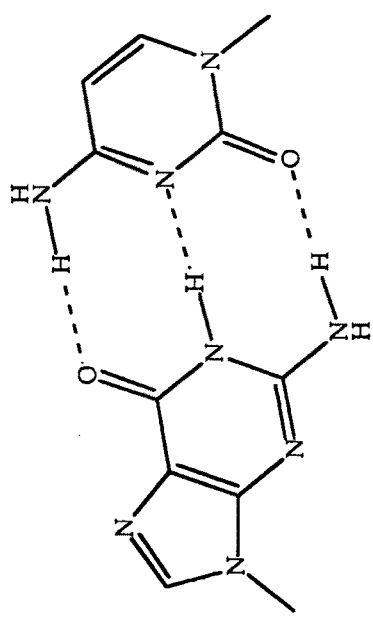 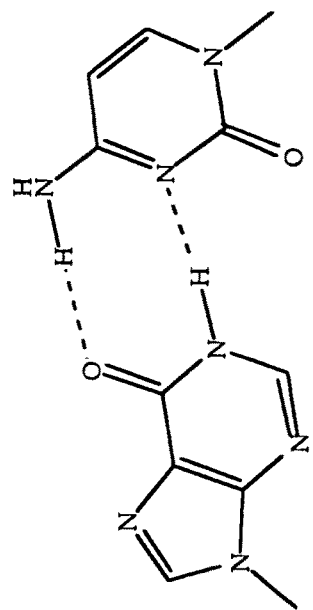 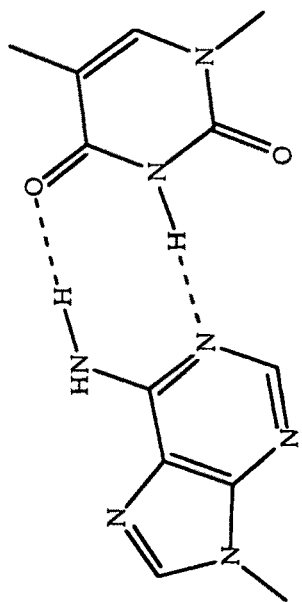 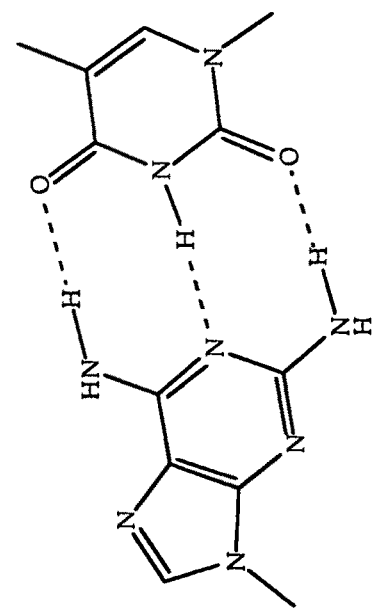
FIG. 6

Base composition of mRNA embedded Alu Sequences amplified by 3DI-PCR

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaarcctaaa rccatrtrta                                              20

<210> SEQ ID NO 2
<211> LENGTH: 22

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taatgtatgg gaattggyty aa                                            22

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgtctagaa gtatcattat ctattggta                                     29

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcggtcgacc aaagcctaaa gccatgtgta                                    30

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggcaggcygg ygccccaggy cagag                                         25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggrrcctctg cggggtrtcg rgcgg                                         25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agayccyggy cyaggcgaca ggaagg                                        26

<210> SEQ ID NO 8
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 8
gcrttgcrcr cttggtttgc gttg                                              24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtcgccaatg ycgaggaggc ccayga                                            26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctccagatca tctrtcctrr tgcttcc                                           27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatgatagaa gaygccaaga acaaygc                                           27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tgcttccttc tggtctctgt rgrgttc                                           27

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cacgcctgta atcccagcac tttggg                                            26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 14
tgtcgcccag gctggagtgc agtgg                                               25

<210> SEQ ID NO 15
<211> LENGTH: 189
<212> TYPE: DNA
<213> ORGANISM: Artificial Sequence
<220> FEATURE:
<223> OTHER INFORMATION: Description of Artificial Sequence: Synthetic
      hypermutated HIV-1 V1V2 region sequence

<400> SEQUENCE: 15
tgcactgatt tgaagaatga tactaatacc aatagtagta gcgggagaat gataatggag         60
aaaggagaga taaaaaactg ctctttcaat atcagcacaa gcataagaga taaggtgcag        120
aaagaatatg cattcttta taaacttgat atagtaccaa tagataatac cagctatagg         180
ttgataagt                                                                189

<210> SEQ ID NO 16
<211> LENGTH: 109
<212> TYPE: DNA
<213> ORGANISM: Artificial Sequence
<220> FEATURE:
<223> OTHER INFORMATION: Description of Artificial Sequence: Synthetic
      poliovirus VP1 segment sequence

<400> SEQUENCE: 16
gtgaaacggt gggggcggca acgtctagag acgctctccc aaacactgaa gccagtggac         60
cagcacactc caaggaaatt ccggcactca ccgcagtgga aactggggc                    109

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide allele of the p21 ras gene
<220> FEATURE:
<221> NAME/KEY: CDS
<222> LOCATION: (1)..(78)

<400> SEQUENCE: 17 atg acg gaa tat aag ctg gtg gtg gtg ggc gcc ggc ggc gtg gga aag           48
Met Thr Glu Tyr Lys Leu Val Val Val Gly Ala Gly Gly Val Gly Lys
1               5                  10                  15 agt gcc ctg acc atc cag ctg acc cag aac ca                                80
Ser Ala Leu Thr Ile Gln Leu Thr Gln Asn
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Thr Glu Tyr Lys Leu Val Val Val Gly Ala Gly Gly Val Gly Lys
1               5                  10                  15

Ser Ala Leu Thr Ile Gln Leu Thr Gln Asn
            20                  25
```

<210> SEQ ID NO 19
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide allele of the p21 ras gene
<220> FEATURE:
<221> NAME/KEY: CDS
<222> LOCATION: (1)..(78)

<400> SEQUENCE: 19

```
atg acg gaa tat aag ctg gtg gtg gtg ggc gcc gtc ggc gtg gga aag      48
Met Thr Glu Tyr Lys Leu Val Val Val Gly Ala Val Gly Val Gly Lys
1               5                   10                  15 agt gcc ctg acc atc cag ctg acc cag aac ca                           80
Ser Ala Leu Thr Ile Gln Leu Thr Gln Asn
            20                  25
```

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Met Thr Glu Tyr Lys Leu Val Val Val Gly Ala Val Gly Val Gly Lys
1               5                   10                  15

Ser Ala Leu Thr Ile Gln Leu Thr Gln Asn
            20                  25
```

<210> SEQ ID NO 21
<211> LENGTH: 148
<212> TYPE: DNA
<213> ORGANISM: Artificial Sequence
<220> FEATURE:
<223> OTHER INFORMATION: Description of Artificial Sequence: Synthetic
      p21 ras gene polynucleotide

<400> SEQUENCE: 21

```
tgacggaata taagctggtg gtggtgggcg ccggcggcgt gggaaagagt gccctgacca      60
tccagctgac ccagaaccag aatataagct ggtggtggtg ggcgccggcg cgtgggaaa     120 gagtgccctg accatccagc tgacccag                                       148
```

<210> SEQ ID NO 22
<211> LENGTH: 148
<212> TYPE: DNA
<213> ORGANISM: Artificial Sequence
<220> FEATURE:
<223> OTHER INFORMATION: Description of Artificial Sequence: Synthetic
      p21 ras gene polynucleotide

<400> SEQUENCE: 22

```
tgacggaata taagctggtg gtggtgggcg ccgtcggcgt gggaaagagt gccctgacca      60
tccagctgac ccagaaccag aatataagct ggtggtggtg ggcgccgtcg cgtgggaaa     120 gagtgccctg accatccagc tgacccag                                       148
```

<210> SEQ ID NO 23
<211> LENGTH: 120
<212> TYPE: RNA
<213> ORGANISM: Artificial Sequence
<220> FEATURE:
<223> OTHER INFORMATION: Description of Artificial Sequence: Synthetic
      measles virus genome polynucleotide

```
<400> SEQUENCE: 23
aagacacucc cuguuguuag gaccuuucuc caaggugaga ggagaguuag uggggguguug     60 uuguagaaca ccaguuuuuc auugagcccu gcuguacguc uaacaacuau gucaagcuca    120

<210> SEQ ID NO 24
<211> LENGTH: 265
<212> TYPE: RNA
<213> ORGANISM: Artificial Sequence
<220> FEATURE:
<223> OTHER INFORMATION: Description of Artificial Sequence: Synthetic
      measles virus genome polynucleotide

<400> SEQUENCE: 24
aagacacucc cuguuguuag gaccuuucuc caaggugaga ggagaguuag uggggguguug     60 uuguagaaca ccaguuuuuc auugagcccu gcuguacguc uaacaacuau gucaagcuca    120
guggccucuu ugaggaguuu ucgggcuuu gcuguggauc ugccaacacc uaagggcagg    180
aacccaaaug cucgcccgau uggaggcccu agggaaucgc uguccucaac aaccccccagc   240 agaaacaugu acauaaagca uucau                                          265

<210> SEQ ID NO 25
<211> LENGTH: 120
<212> TYPE: RNA
<213> ORGANISM: Artificial Sequence
<220> FEATURE:
<223> OTHER INFORMATION: Description of Artificial Sequence: Synthetic
      Rift Valley fever virus genome polynucleotide

<400> SEQUENCE: 25
aaugaacuga uguccuugua augggcuggc ccaaagagau ugacaucaga uguaucaaaa     60
gauuccaucu cguaaggacc acuaacaucc aacucuaugc aauuaacaac augacugaau    120

<210> SEQ ID NO 26
<211> LENGTH: 199
<212> TYPE: DNA
<213> ORGANISM: Human immunodeficiency virus type 1

<400> SEQUENCE: 26
aaattaaccc cactctgtgt tagttttaaag tgcactgatt tggggaatgc tactaatacc     60
aatagtagta ataccaatag tagtagcggg gaaatgatga tggagaaagg agagataaaa   120
aactgctctt tcaatatcag cacaagcata agaggtaagg tgcagaaaga atatgcattt    180
ttttataaac ttgatataa                                                 199

<210> SEQ ID NO 27
<211> LENGTH: 265
<212> TYPE: RNA
<213> ORGANISM: Measles virus

<400> SEQUENCE: 27
aagacacucc cuguuguuag gaccuuucuc caaggugaga ggagaguuag uggggguguug     60 uuguagaaca ccaguuuuuc auugagcccu gcuguacguc uaacaacuau gucaagcuca    120
guggccucuu ugaggaguuu ucgggcuuu gcuguggauc ugccaacacc uaagggcagg    180
aacccaaaug cucgcccgau uggaggcccu agggaaucgc uguccucaac aaccccccagc   240 agaaacaugu acauaaagca uucau                                          265

<210> SEQ ID NO 28
<211> LENGTH: 257
```

-continued

```
<212> TYPE: RNA
<213> ORGANISM: Rift Valley fever virus

<400> SEQUENCE: 28
ugaagagaac cuuugauaaa ucauagucuu ugcuggagca ccgaccuguu ucuagaacuu      60
uccuaacuga ggcucucccc aucuuagaaa uagcauaauc aacaaacuua uccauuaagg     120
gaugagcaau cauugauaau gaacugaugu ccuuguaaug ggcuggccca aagagauuga     180
caucagaugu aucaaaagau uccaucucgu aaggaccacu aacauccaac ucuaugcaau     240
uaacaacaug acugaau                                                   257
```

DIFFERENTIAL AMPLIFICATION OF MUTANT NUCLEIC ACIDS BY PCR IN A MIXTURE OF NUCLEIC ACIDS

CROSS-REFERENCE TO RELATED APPLICATIONS

This application is a national phase application of International Application No. PCT/IB2006/004187, filed Dec. 28, 2006, which claims priority of U.S. patent application Ser. No. 11/321,048, filed Dec. 30, 2005, now abandoned, the contents of both of which are incorporated herein by reference.

FIELD OF THE INVENTION

The present invention relates to the differential amplification of nucleic acids, especially, mutant nucleic acids, by polymerase chain reaction (PCR) in a mixture of nucleic acids. More particularly, this invention relates to preferentially amplifying copies of one or more nucleic acid having a specific AT, or having a specific GC composition, for example one or more mutant nucleic acids which is (are) regarded as a target for amplification, in a mixture of nucleic acids, said mixture possibly containing also the parental nucleic acid of the mutant nucleic acids in order to enrich the mixture in copies of the mutant nucleic acids.

BACKGROUND OF THE INVENTION

The identification and characterization of particular alleles or of mutations have been historically important in every branch of biology and medicine. The study of mutations has contributed significantly to the understanding of the mechanisms and pathways of both normal physiological processes as well as disease pathogenesis. It has now moved on to the study of the relationships between protein structure and function, and correlation between genotype and disease phenotype.

Various developments in molecular genetics and biology have revolutionized the ability to analyze genes at a nucleotide sequence level. The emerging constraint on advances in molecular pathology appears to be the ability to correlate mutant genotype with disease phenotype.

Accordingly, there exists a need in the art to detect small mutations or polymorphisms, involving alterations to one or several bases in a nucleic acid sequence. More particularly, there exists a need in the art to selectively and preferentially produce copies of mutant nucleic acids in mixtures, said mixture possibly also containing the parental nucleic acid so that the mutant nucleic acids can be further analyzed. To these ends, methods should enable the rapid analysis of specific sequences, with decreasing requirements on sample quality and quantity, time, and manual effort.

SUMMARY OF THE INVENTION

Accordingly, this invention aids in fulfilling this need in the art. One embodiment of this invention provides a method for enriching a mutant nucleic acid in a mixture of nucleic acids. The method comprises (a) providing a nucleic acid mixture comprising a parental nucleic acid and a mutant nucleic acid of the parental nucleic acid; and (b) amplifying the nucleic acids in the nucleic acid mixture by polymerase chain reaction (PCR). The mutant nucleic acid is an AT-rich nucleic acid variant of the parental nucleic acid. The AT-rich nucleic acid variant is denatured and selectively amplified by carrying out PCR using a denaturation temperature 1-3° C. lower than the lowest denaturation temperature ($T_p$ or $T_d$) that allows amplification of the parental nucleic acid. The mutant nucleic acid is thereby enriched in the nucleic acid mixture. In one embodiment, the G→A mutant of the parental nucleic acid pairs with a fully complementary nucleic acid sequence to form the AP-rich nucleic acid variant.

This invention also provides a method for enriching a mutant nucleic acid in a mixture of nucleic acids, wherein the method comprises: (a) providing a nucleic acid mixture comprising a parental nucleic acid and a mutant nucleic acid of the parental nucleic acid; and (b) amplifying the nucleic acids in the nucleic acid mixture by polymerase chain reaction (PCR). The mutant nucleic acid in this embodiment is a GC-rich nucleic acid variant of the parental nucleic acid. The GC-rich nucleic acid variant is denatured and selectively amplified by carrying out PCR using a denaturation temperature 1-3° C. lower than the lowest denaturation temperature ($T_p$ or $T_d$) that allows amplification of the parental nucleic acid, to thereby enrich the mutant nucleic acid in the nucleic acid mixture. PCR is carried out in a reaction medium containing deoxyinosine triphosphate (dITP), or in a reaction medium containing 2,6-diaminopurine triphosphate (dDTP), or in a reaction medium containing dITP and dDTP.

The methods of the invention can include an optional step of detecting the products of the PCR. In addition, the PCR can be carried out in the absence of the parental nucleic acid.

BRIEF DESCRIPTION OF THE DRAWINGS

This invention will be described in greater detail with reference to the drawings in which:

FIG. 2 depicts a collection of G→A-hypermutated HIV-1 V1V2 region sequences derived from Δvif stock virus grown on 293T cells [293T/PBMC, FIG. 1(a-c)]. For clarity, only a 189 bp region of the 304 bp segment that was amplified is shown. Sequences are aligned with respect to the parental sequence. Only differences are shown. Hyphens denote gaps. Clone designation is shown to the left. Analysis of material from the 95° C. amplification failed to identify any hypermutated genomes.

FIG. 3 depicts a collection of AT-rich poliovirus VP1 segments derived from a patient with post-vaccinal acute flaccid paralysis. For clarity, only a 109 bp region of the 480 bp segment that was amplified is shown. Sequences are aligned with respect to poliovirus Sabin 1. Only differences are shown. Clone designation is shown to the right. The 3D-PCR-amplified segments bore one to six GC→AT transitions compared with Sabin 1. Analysis of material from the 95° C. amplification yielded two substitutions among 17 clones in the same sequence.

FIG. 4A depicts the sequences of two alleles of the p21 ras gene. Primers are underlined in the Figure.

FIG. 4B depicts primers for amplifying a 19 bp window of the p21 ras gene.

FIG. 6. Base pairing of standard DNA base pairs as well as the modified bases, Inosine (I) and 2,6-Diaminopurine (D), that allow inversing the natural 3:2 hydrogen bonding rule.

FIG. 10. Sequences of the seven molecular clones used to calibrate midpoint denaturation temperatures. The 3, 6, 9, 12, 15 and 23 G→A transitions distinguishing them from the reference sequence, defined as "0", are shown on the right. They represent segments of the human immunodeficiency type 1 (HIV-1) env gene, notably the V1V2 hypervariable regions and were derived from an in vitro study of APOBEC3G editing (10). Amplification primers were RT3 5'GCGTCTAGAAGTATCATTATCTATTGGTA and RT4 5'GCGGTCGACCAAAGCCTAAAGCCATGTGTA.

Figure 11A:
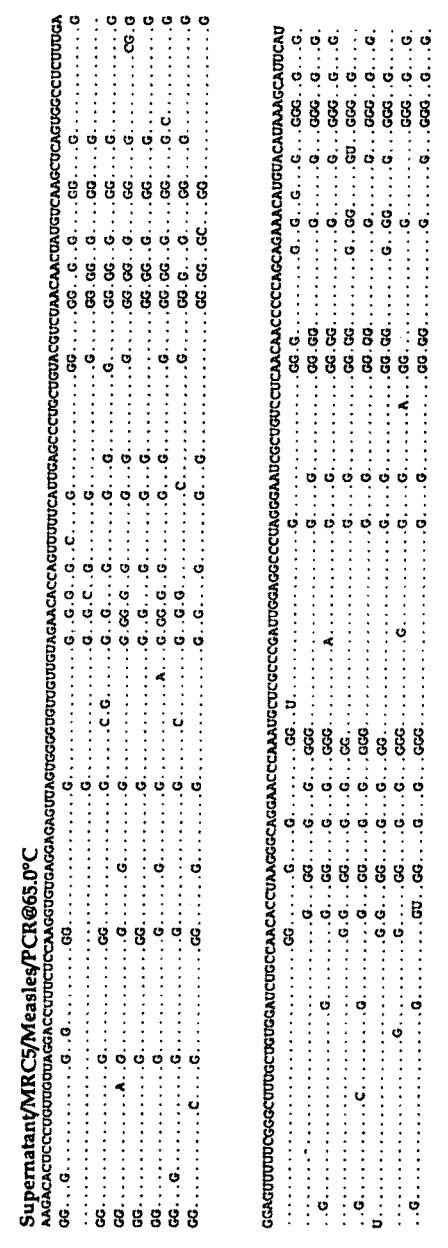
Figure 11B:
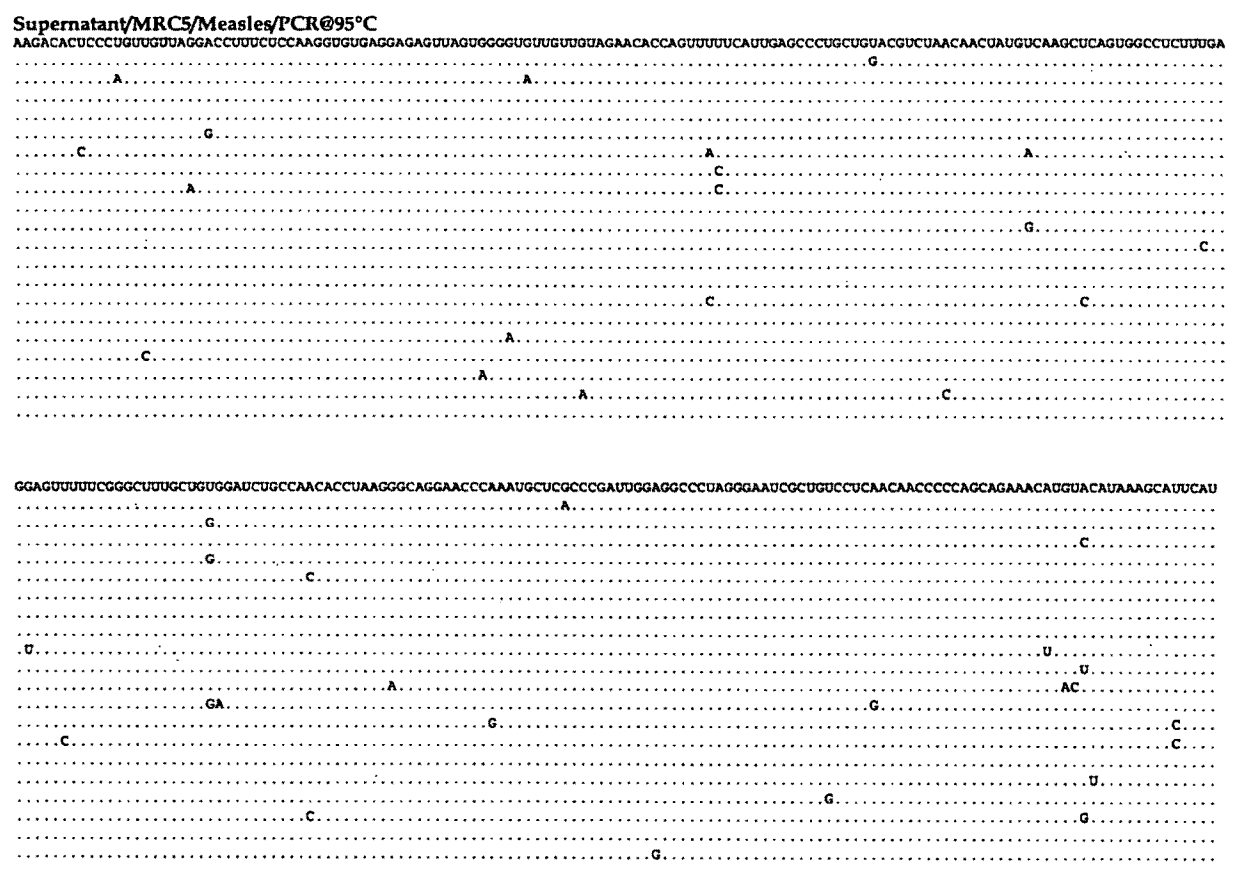
Figure 11C:
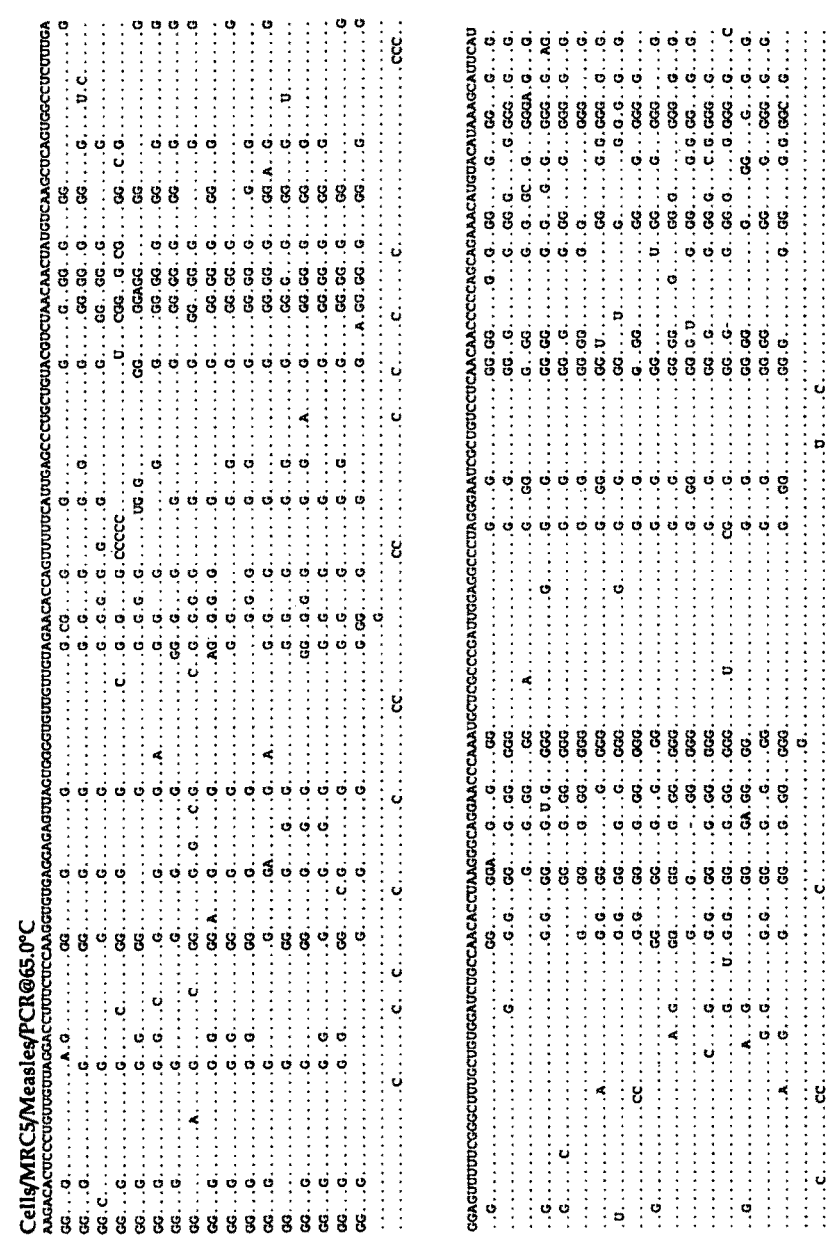
Figure 11D:
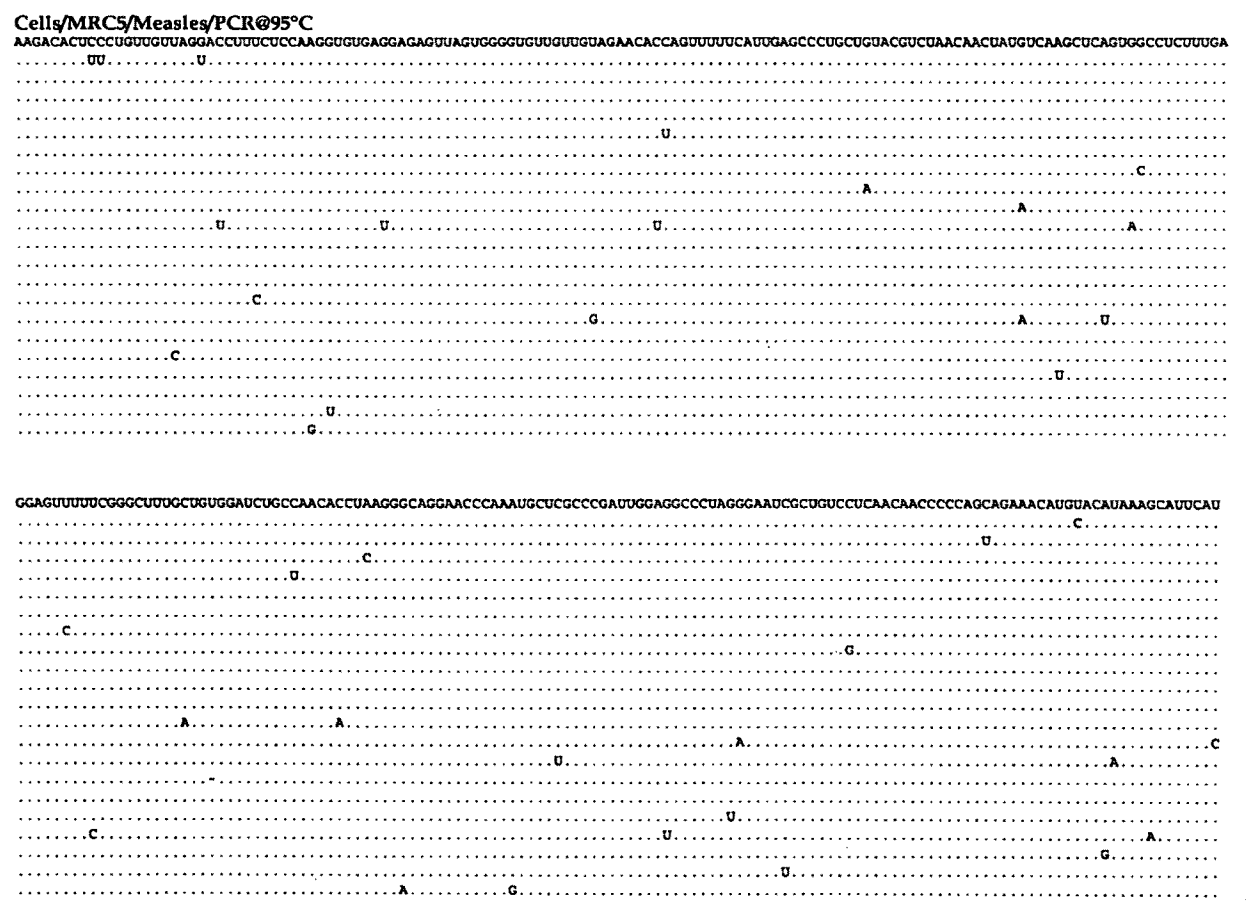
Figure 11E:
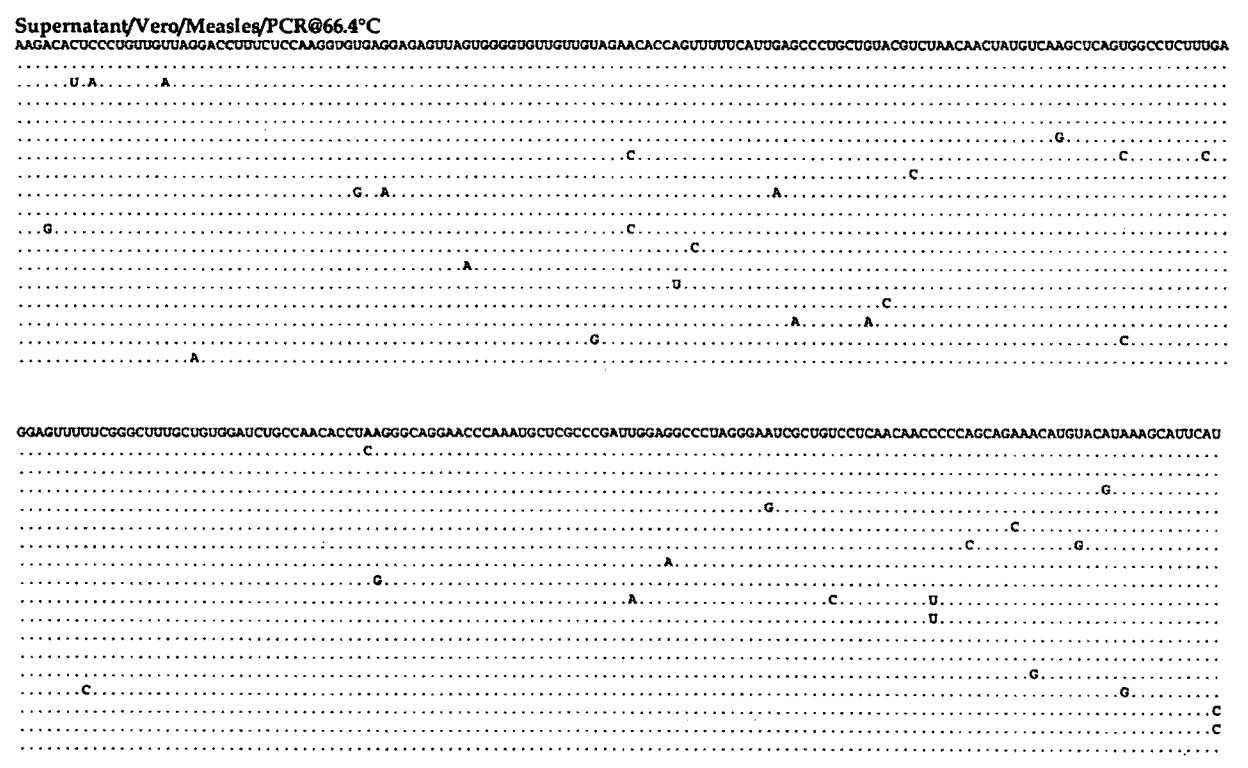
Figure 11F:
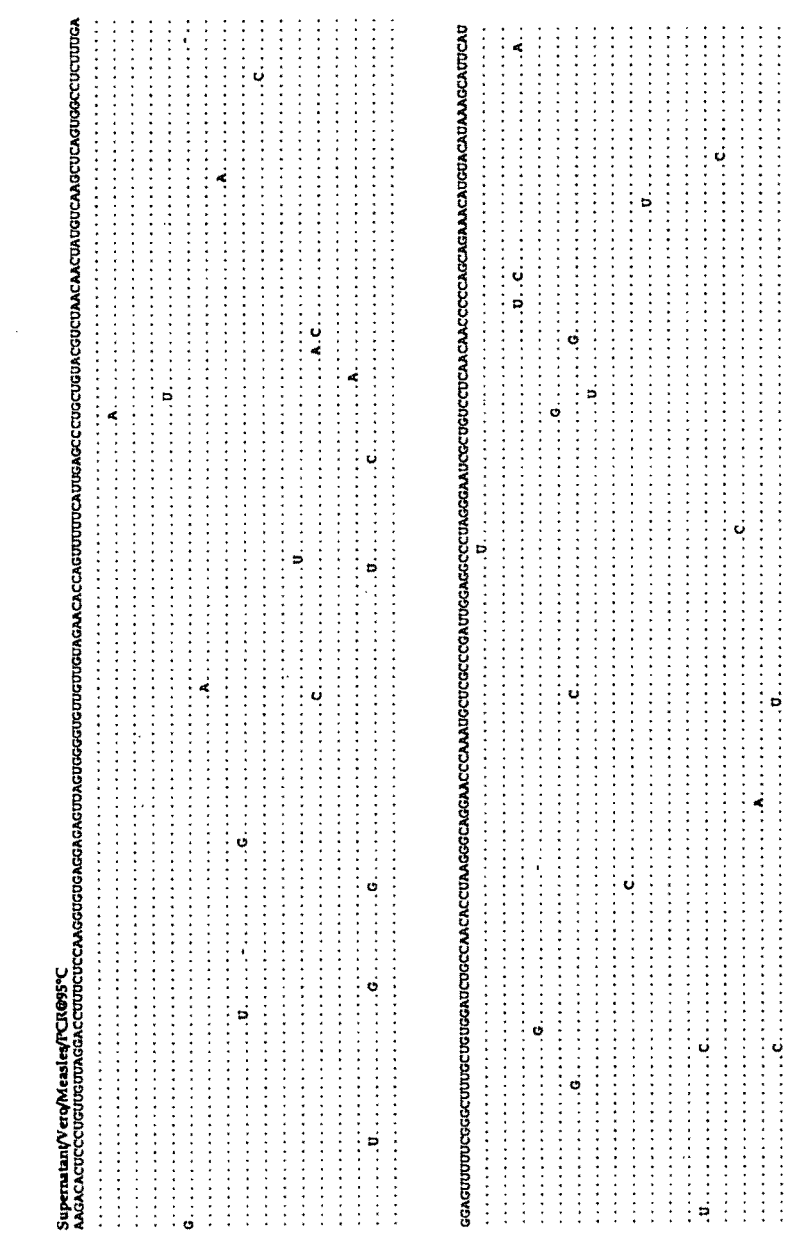
Figure 11G:
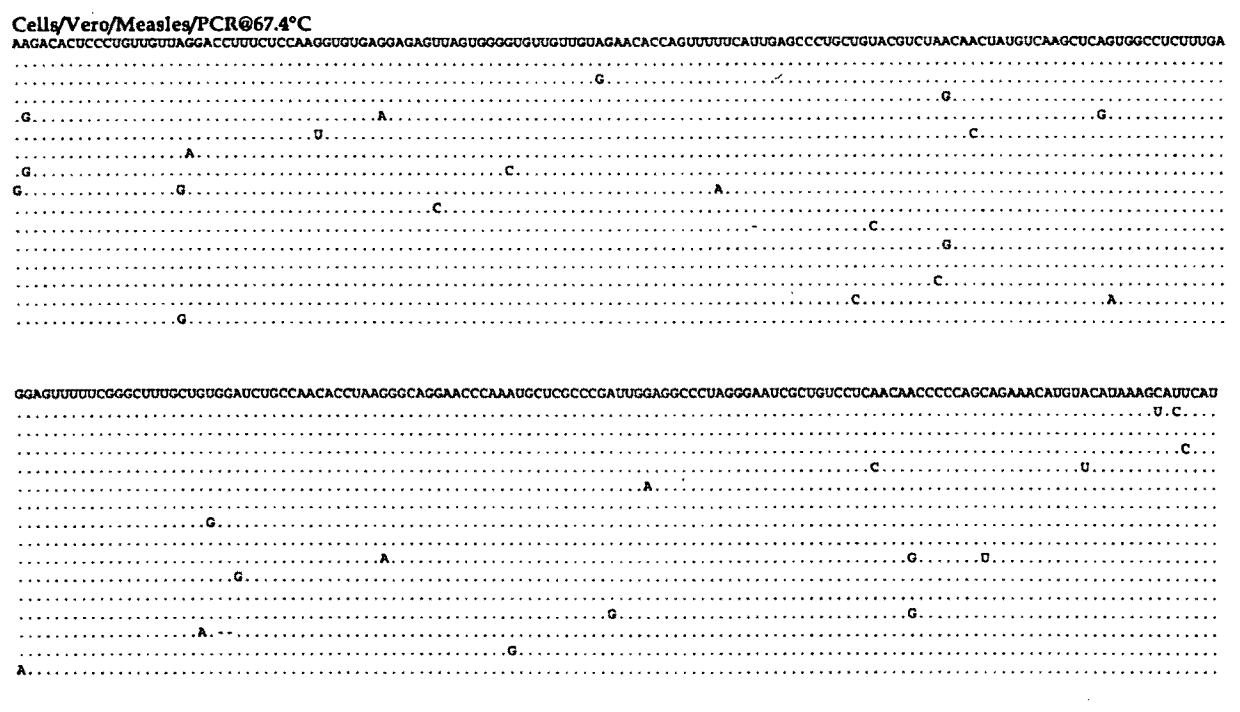
Figure 11H:
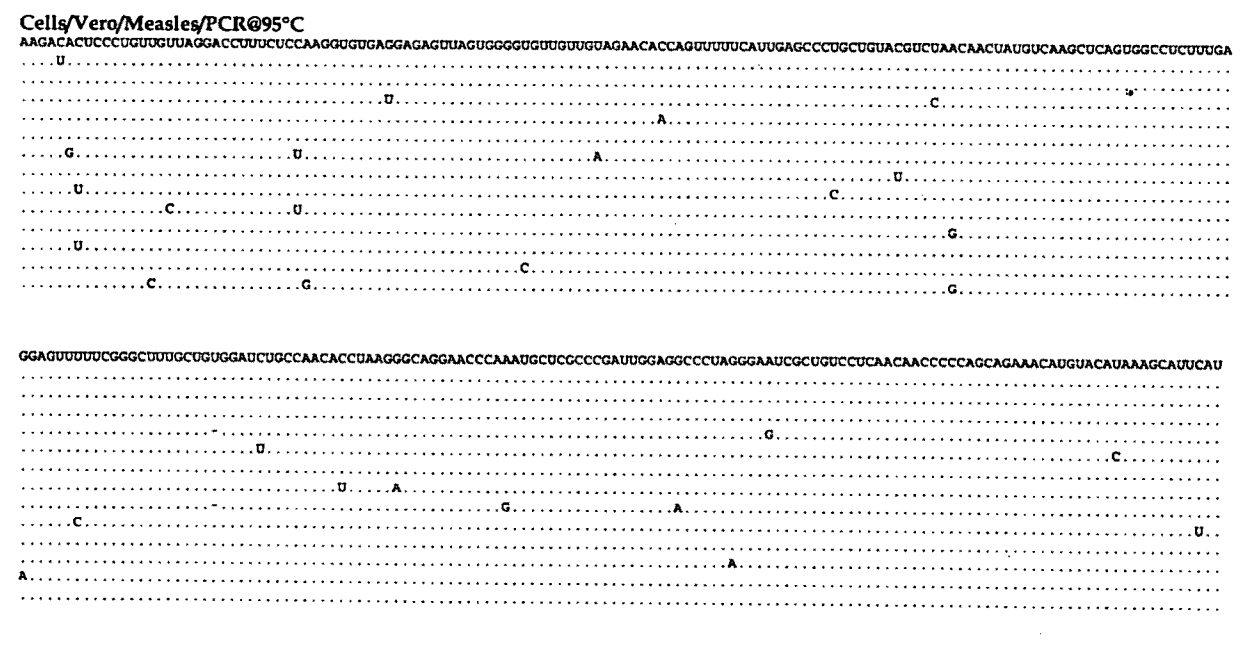

FIG. 11. Complete MV sequence sets. Only differences with respect to the Schwarz reference sequence are shown.

FIG. 12. Complete RVFV sequence sets. Only differences with respect to the RVFV clone 13 reference sequence are shown. When a sequence was found more than once the frequency is given to the right of the sequence.

DETAILED DESCRIPTION OF THE INVENTION

Figure 1:
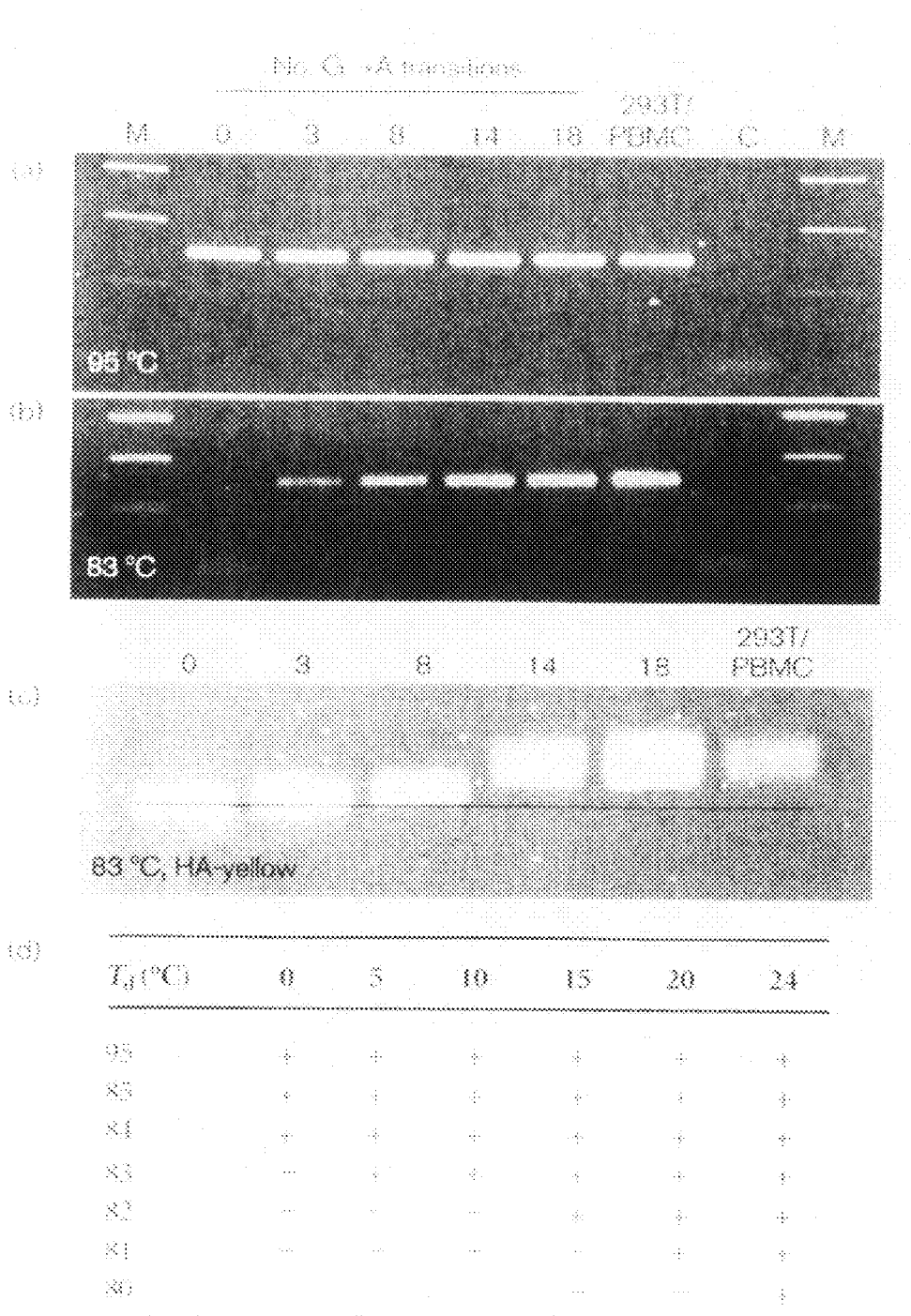
FIG. 1 depicts differential DNA denaturation amplification of G→A-hypermutated HIV-1 genomes. (a) Four sequences harbouring 3, 8, 14 and 18 G→A transitions compared with the reference sequence (0) were amplified under standard PCR conditions with a denaturation temperature of 95° C. M and C denote molecular mass markers and negative control, respectively. 293T/PBMC refers to material amplified from PBMCs infected by an HIV-1Δvif virus stock produced by transfection of 293T cells. (b) The same samples as in (a) were amplified with a denaturation temperature of 83° C. (c) The same PCR products as in (b) were electrophoresed in agarose gel with 1 U HA-yellow (ml agarose)$^{-1}$. The material for the wild-type control (0) that was not amplified at 83° C. came from lane 0, FIG. 1(a). The black line was added to help to visualize the retardation of AT-rich DNA due to HA-yellow. (d) The relationship between denaturation temperature ($T_d$) and selective amplification was explored by using another series of clones with 0, 5, 10, 15, 20 and 24 G→A transitions with respect to the reference sequence (0).
Figure 5:
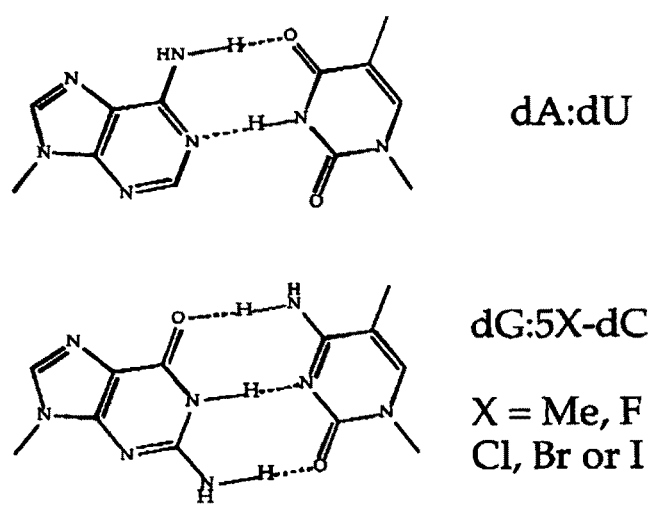
FIG. 5 depicts the chemical structure of dUTP and dCTP analogues that can optionally be substituted for dTTP.

It is one of the truisms of genetics that adenosine (A) pairs with thymine/uracil (T/U) while guanosine (G) pairs with cytidine (C). Pairing involves non-covalent hydrogen bonds, two for the A:T pair, three for the G:C pair.

Virus genomes from the same family may exhibit a wide range in their DNA GC content, whereas viral hypermutants differ substantially in GC content from their parental genomes. As AT-rich DNA melts at lower temperatures than GC-rich DNA, use of a lower denaturation temperature during PCR should allow differential amplification of AT-rich genomes or variants within a quasispecies. From this experimental observation, initially carried out on viral genomes, a more generally applicable method has been derived, in order to selectively amplify AT-rich nucleic acids in a sample. The latter situation has been explored explicitly in a two-step process by using a series of well-defined viral sequences differing in their AT content. Firstly, the lowest denaturation temperature ($T_p$) that allowed amplification of the parental sequence was determined. Secondly, differential amplification of AT-rich viral variants was obtained by using a denaturation temperature 1-3° C. lower than $T_p$. Application of this sensitive method to two different viruses made it possible to identify human immunodeficiency virus type 1 G→A hypermutants in a situation where none were expected and to amplify AT-rich variants selectively within a spectrum of poliovirus mutants.

Thus, method according to this invention allows differential amplification of DNA segments differing by one to many GC→AT transitions. As the degree of substitution directly impacts the melting temperature of the DNA, the lower the denaturation temperature the more substituted the genomes amplified. As different loci may have widely different base compositions the conditions can be optimized for each segment. This observation originally made on viral nucleic acids has furthermore been extended to nucleic acids of other sources, including bacterial or cellular nucleic acid, including human genes. The method of the invention thus applies to DNA including genomic DNA, or to cDNA (reverse transcribed RNA) no matter the origin. Suitable sources of nucleic acids are viruses, either DNA or RNA viruses, especially negative RNA viruses, or retroviruses. The RNA negative viruses are segmented or non segmented viruses. Examples are HIV-1, HIV-2, poliovirus, and measle virus. Other sources of nucleic acids are other pathogenic organisms such as bacteria. The invention can also be carried out on cellular nucleic acids, or on nucleic acid characteristic of a tumor associated antigen.

In its broadest sense, this invention relates to the amplification of segments of DNA by the polymerase chain reaction (PCR). As used herein, the terms "polymerase chain reaction" and "PCR" are used in their conventional sense as an in vitro method for the enzymatic synthesis of specific DNA sequences using two oligonucleotide primers that hybridize to opposite strands and flank the region of interest in a target DNA. A repetitive series of cycles involving template denaturation, primer annealing, and the extension of the annealed primers by DNA polymerase results in the exponential accumulation of a specific fragment whose termini are defined by the 5' ends of the primers. Because the primer extension products synthesized in one cycle can serve as templates in the next cycle, the number of target DNA copies approximately doubles at every cycle. The use of the thermostable DNA polymerase, such as Taq polymerase isolated from *Thermus aquaticus* or variant or related Taq polymerases, makes it possible to carry out the PCR reaction of the invention in a simple and robust manner, which can be automated using a conventional thermal cycling device.

The PCR reaction of the invention can be carried out using conventional reaction components, such as, the template DNA, primers, Taq or another polymerase, dNTP's, and buffer. The reaction can be carried out in the conventional manner by simply cycling the temperature within a reaction chamber. The specificity and yield of the amplification reaction can be regulated by controlling well-known parameters, such as enzyme, primer, dNTP, and $Mg^{++}$ concentrations, as well as the temperature cycling profile.

Because of the wide variety of applications in which PCR is used according to the invention, it is not possible to describe a single set of conditions for all situations. The amplification can be initially performed in a DNA Thermal Cycler (Perkin-Elmer Cetus Instruments) using the "Step-Cycle" program and reagents recommended by the manufacturer. For any given pair of oligonucleotide primers an optimal set of conditions can then be established.

Once the reagents and the step-cycle program have been established for the target nucleic acid sequence being amplified, the lowest denaturation temperature that allows amplification of the parental sequence is determined. This lowest denaturation temperature is termed $T_p$. Differential amplification of either AT-rich nucleic acid variants (also designated alleles) or in another aspect of the invention GC-rich nucleic acids variants (also designated alleles), is obtained by using the same reagents for AT-rich nucleic acids or different hereinafter described reagents for GC-rich nucleic acids, and the same step-cycle program, except that the denaturation temperature for each cycle of PCR is about 1 to 10° C., especially about 1 to 6° C., and more particularly, about 1 to 3° C., preferably 1° C., lower than $T_p$. Thus, the temperature employed for the denaturation step of PCR will be a temperature at which the mutant nucleic acid is preferentially amplified relative to the parental nucleic acid. Preferential amplification can be determined, for example, by gel electrophoresis or by direct sequencing of PCR products or by detection with a labeled probe.

The nucleic acid mixture employed in the methods of the invention can comprise a parental nucleic acid and/or at least one mutant nucleic acid of the parental nucleic acid. In a first embodiment, the mutant nucleic acid can contain at least one G→A mutation relative to the parental nucleic acid to form, after base pairing, an AT-rich nucleic acid variant of the parental nucleic acid. In another embodiment, the mutant nucleic acid can contain at least one A→G mutation relative to the parental nucleic acid to form, after base pairing, a GC-rich nucleic acid variant of the parental nucleic acid. It will be understood that the mixture can contain a mutant nucleic acid having both G→A and A→G mutations at different loci, or the mixture can contain two or more nucleic acid mutants each containing either one or more mutations or one or more A→G mutations. The number of mutations in the mutant nucleic acids is typically 1-18 mutations compared to the parental nucleic acid.

The methods of the invention apply to any DNA or cDNA (reverse transcribed RNA) fragment no matter the origin. An important property of the PCR reaction of the invention, particularly in diagnostic applications, is the capacity to amplify a target sequence from crude DNA preparations as well as from degraded DNA templates. The DNA in the sample to be amplified need not be chemically pure to serve as a template provided that the sample does not contain inhibitors of the polymerase. The ability to amplify specific sequences from crude DNA samples has important implications for research applications, for medical diagnostic applications, and for forensics.

The primers used in PCR can contain mismatches relative to the sequences to which they base-pair. For example, the primers can be degenerate, as is described for primers SK122/SK123 used to hybridize with the V1V2 region of the HIV-1 envelope gene in the Examples hereinafter. If the primers contain mismatches relative to the sequence to which they base-pair, the hybridization step of PCR can be optimized independently of the denaturation step of PCR. In addition, it will be understood that the primers can contain mismatches relative to the parental sequence.

The length of the primers has not been found to be critical in carrying out the methods of the invention. Standard length primers can be employed, and optimal primer length can be determined by routine experimentation. Typically, the primers will be about 20-25 bp, but may be longer or shorter.

Similarly, the length of the parental sequence has not been found to be critical in carrying out the methods of the invention. Typically, the parental sequence will be up to about 500 bp especially has from about 40 to about 500 bases. It will be understood that longer or shorter sequences can be employed.

Further, the size of the targeted mutant nucleic acids being amplified has not been found to be critical in the methods of the invention. Mutant nucleic acids up to about 500 bp can be employed, although it will frequently be more convenient to use shorter sequences.

The region of the mutant nucleic acids being amplified, also referred to as the window between the two primers, can vary depending upon the target nucleic acids. For example, the region amplified can comprise about 20, 30, 40, 50, 60 bp, or 80 bp although longer or shorter sequences are contemplated by the invention. Amplified regions of 19 and 30 bp are described for p12 ras gene in the Examples hereinafter.

In some cases, the amplified region may affect the manner in which the amplified nucleic acids are detected. For example, to detect a single point mutation, the window between two primers can be 3-12 nucleotides, but in this case, using 20 bp primers, the bands of the PCR products are about 43-52 base pairs. Nucleic acid molecules of this size can not readily be detected by electrophoresis in agarose gel, but they can be detected in polyacrylamide gel.

In any event, the detection method can be adapted to the characteristics of the amplified PCR product. Preferred detection methods are gel electrophoresis in agarose or acrylamide gel, capillary electrophoresis, or chromatography, especially gel filtration or ion-exchange chromatography.

The methods of this invention have a wide variety of uses. For example, the methods can be employed to characterize the origin of parental DNA or to detect mutations characteristic of human gene disorders. The methods can also be employed for detecting G→A mutant strains of HIV, particularly G→A hypermutants, that are resistant to anti-retroviral drugs. Further, the methods of the invention can be employed for detecting neurovirulent vaccine-derived poliovirus isolates that cause vaccine-associated paralytic poliomyelitis. For bibliographic references about the nucleotide variation of vaccine strains of poliovirus see Buttinelli et al, J. Gen. Virol. 2003, 84, 1215-1221 and Georgescu et al., J. Virol. 1997, 71, 7758-7768. In a preferred embodiment of the invention, the methods of the invention are used to amplify parental and mutant nucleic acids from measle virus.

It will be understood that the methods of the invention are useful for detecting specific mutations at specific sites, which have previously been characterized and sequenced. The methods of the invention are also useful for detecting the presence of unknown sequence differences in a given length of DNA. The methods are useful for detecting known mutations, and are particularly useful for rapidly detecting multi-allelic loci. It will be understood that the methods of the invention can also be used to amplify sequences containing small deletions, such as 1 or 2 bp deletions.

Although the method allows differential amplification, it is not quantitative per se. However, coupled to limiting dilution of input DNA it is possible to quantitate the fraction of AT rich genomes within a sample. Alternatively, Taqman PCR can be performed at 95° C. and the selective temperature to determine the copy number per sample. The ratio of the two values can give the relative concentration of AT-rich alleles with respect to the total concentration of all alleles.

The methods according to the invention encompass variants that use modified bases that can influence slightly the melting temperature of DNA. For example, dUTP can be used to replace dTTP (FIG. 5). The difference will be small. In the same vein, one can use modified derivatives of dCTP, such as 5-methyl dCTP, 5-fluoro dCTP, 5-chloro dCTP, 5-bromo dCTP, or 5-iodo dCTP, which can be incorporated into DNA by Taq polymerase or another thermostable DNA polymerase (FIG. 5). These dCTP analogues are particularly interesting, for when incorporated into DNA, the DNA melts to higher temperatures (Hoheisel et al., 1990, Wong et al., 1991). Accordingly, use of any one of these modified bases will enhance the discrimination between the parental sequence and AT rich allele.

Equally, the methods of the invention encompass the use of non-standard PCR buffer conditions, particularly the use of certain salts and salt concentrations and the use of organic molecules. It is well known that the denaturation temperature can be influenced by the nature of the ion and ionic strength, for example tetraethylammonium chloride (Muraoka et al., 1980) and the use of small organic molecules, such as methanol or polyethylene glycol, to cite just two (Muraoka et al., 1980, Votavova et al., 1986).

The methods of the invention can be used to detect small deletions in an allele. The melting temperature is a function of the number of hydrogen bonds distinguishing two alleles. Deletion of a single base will remove 2 or 3 hydrogen bonds, and hence will melt to lower temperature. Larger deletions will be detected more readily. Hence, the method of the invention can be used to selectively amplify alleles with small deletions, for example, mitochondrial DNA or microsatelites associated with a disease susceptibility gene, although these are mentioned as examples and not to limit the invention.

By reducing the size of the region to be amplified of the targeted nucleic acid, i.e., the size of the PCR fragment to 60-80 bases, alleles differing by a single GC→AT substitution can be differentially amplified. Hence, the method of the invention can be used in the search for single nucleotide polymorphisms (SNPs). Being temperature based, no allele specific oligonudeotides are necessary.

As the window of observation is generally between 10-30 bases (60-80 bp-2×25 bp primers), the method of the invention can detect any mutation provided that it reduces the melting temperature of the allele. As GC→AT substitutions represent the most frequent substitutions (40-50%) characterizing human gene disorders, p53 inactivating mutations or those of pseudogenes compared to the orthologous gene, it is possible to apply the method of the invention to the detection of a mutation characteristic of a pre-tumourous cell in a blood sample or in the characterization of human genotypes via SNP typing.

The methods of the invention, designated "3DPCR" (for Differential DNA Denaturation—PCR), can be used to selectively amplify AT rich alleles from the normal counterpart. This follows on from the fact that an A:T base pair involves 2 hydrogen bonds, while a G:C pair involves 3 (FIG. 1). Consequently, it has been demonstrated that the denaturation temperature of an AT rich allele will be slightly lower than that of the normal counterpart. The converse, the selective amplification of a G:C rich allele compared to a normal counterpart, is not amenable to analysis by 3DPCR because it would melt to a higher temperature than the normal allele, and at higher temperatures both the normal and GC rich alleles will be amplified.

This invention provides another method that addresses this problem. Deoxyinosine triphosphate (dITP) can be substituted for dGTP in PCR designed for selective amplification of GC-rich nucleic acids, especially GC-rich alleles compared to a nucleic acid, especially an allele of reference. Inosine lacks the amino group at position 2 compared to guanosine. As a consequence, dITP forms only 2 hydrogen bonds with dCTP (FIG. 5). Hence, the specificity of base pairing is preserved (G or I pairs with C), and with it the information, while the number of hydrogen bonds is reduced from 3 to 2. By contrast, 2,6-diamino purine (D) bears an additional amino group compared to adenosine (2-aminopurine). Furthermore, it base pairs with thymidine via 3 hydrogen bonds (FIG. 5). Again the information content is preserved (D or A pairs with T). Accordingly dDTP may be used to substitute dATP in differential PCR designed for selective amplification of GC-rich nucleic acids, especially alleles compared to a nucleic acid, especially an allele of reference.

In a particular aspect of the invention, the selective amplification enables amplification of GC-rich mutants or hypermutants of a reference nucleic acid.

Thus, while it is known that dDTP and dITP can substitute for dATP and dGTP respectively in a PCR reaction, indeed both can be used in the same reaction, PCR material so derived will have the inverse melting properties compared to products bearing the canonical bases, dATP and dGTP. G:C rich alleles, (I:C in fact, 2 hydrogen bonds) will melt to slightly lower temperatures than the normal A:T allele (D:T in fact, 3 hydrogen bonds).

Accordingly, performing 3DPCR of the invention with these modified bases allows selective amplification of A:T rich nucleic acids, especially alleles, and performing 3DIPCR allows selective amplification of C:G rich nucleic adds, especially alleles. The invention thus concerns the use of a lower melting temperature to amplify a subset of nucleic acids, especially alleles, that can be distinguished by a fractionally lower DNA melting temperature. Accordingly, this invention also involves the use of dDTP and dITP as a means to convert a G:C rich allele into DNA that melts at a lower temperature. This method of the invention is termed "inverse 3DPCR" or "i3DPCR" or "3DIPCR" to emphasize that it allows amplification of G:C rich alleles as opposed to A:T rich alleles, which 3DPCR does.

There is much renewed interest recently in adenosine deamination of viral RNA. This results from editing of adenosine residues in RNA by an interferon induced host cell enzyme, ADAR, and its isoforms. The enzyme deaminates A to yield inosine (I). When repeated, this gives rise to A→G hypermutants for, as mentioned above, I pairs as G.

The invention thus relates to a method for in vitro enriching a GC-rich nucleic acid, in a mixture of nucleic acids, wherein, if present, the GC-rich nucleic acid, is a GC-enriched nudeic acid with respect to a parental nudeic acid, wherein the method comprises:

(a) providing a nucleic acid mixture comprising said parental nucleic acid and a GC-rich nucleic acid of said parental nucleic acid;

(b) carrying out differential amplification of the nucleic acids in the nucleic acid mixture by polymerase chain reaction (PCR) wherein, for said differential amplification the GC-rich nucleic acid is denatured and selectively amplified by carrying out PCR using a denaturation temperature 1-10° C., for example 1-6° C. especially 1-3° C. lower than the lowest denaturation temperature ($T_p$) that allows amplification of the parental nucleic acid, to thereby amplify the GC-rich nucleic acid in the nucleic acid mixture;

and said differential PCR is carried out in a reaction medium containing deoxyinosine triphosphate (dITP), or in a reaction medium containing deoxy 2,6-diaminopurine (dDTP), or in a reaction medium containing dITP and dDTP; and (c) optionally detecting the products of the PCR.

The expression "GC-enriched nucleic acid" means that the composition of said nucleic add in G and C nucleobases is increased with respect to that of the parental nucleic acid, as a result of substitution of A, T, and/or U nucleobases for G and/or C nudeobases with respect to the parental nucleic acid.

According to a particular embodiment of the invention, the GC-rich nucleic acid is a mutant nucleic acid with respect to the parental nucleic acid.

According to a particular embodiment, the method of the invention to amplify (enrich) a GC-rich nucleic acid (especially a GC-rich mutant or variant or allele) in a mixture of nucleic acids, is such that the above disclosed step a) comprises:

(i) optionally carrying out a step of reverse transcription and/or optionally a step of standard amplification, e.g., PCR amplification to enrich the mixture in parental and GC-rich nucleic acids (especially a mutant or a variant or an allele) and, (ii) converting, especially by a PCR reaction, the DNA of said nucleic acid mixture (starting DNA) into DNA wherein Guanine bases (G) are converted into Inosine bases (I) and Adenosine bases (A) are converted into to 2,6-diaminopurine bases (D).

According to a particular embodiment of this method of the invention, differential amplification is carried out using equimolar ratio of dTTP, dCTP, dDTP and dTTP.

According to a particular embodiment of this method the suitable polymerases for carrying out amplifications are Taq polymerase or variants thereof such as those exemplified in the present application.

In another particular embodiment of the method of the invention, the mixture of nucleic acids is devoid of said parental nucleic acid corresponding to the GC-rich nucleic acid to be enriched especially to the GC-rich mutant, variant or allele of the parental nucleic acid.

The following conditions represent an example of suitable buffer conditions for amplification: 2.5 mM MgCl2, 50 mM KCl, 10 mM Tris-HCl (pH 8.3), 200 µM of each primer and 5 U of Taq DNA polymerase or a variant thereof in a final volume of 50 µl. More generally, PCR amplifications are carried out in conditions well know from the skilled person, as detailed in the following examples and also disclosed in the literature such as in Maniatis (Molecular Cloning).

A particular embodiment of the disclosed method for enriching (amplifying) a nucleic acid mixture in CG-rich mutants, variant or allele of a parental nucleic acid encompasses a method as disclosed herein, wherein differential amplification is carried out on a fraction of the DNA material obtained as a result of the conversion step.

According to a particular embodiment of the method of the invention, the differential amplification is carried out in PCR conditions enabling temperature gradients to be generated in denaturation temperature, in order to enable amplification of a CG-rich nuelic acid selectively with respect to amplification of the corresponding parental nucleic acid.

In order to determine the denaturation temperature that enables the selective amplification, of the GC-rich nucleic acid with respect to the corresponding parental nucleic acid, the denaturation temperature of the parental nucleic acid must be known or must be determined.

According to a particular embodiment of the invention, the parental nucleic acid is present within the nucleic acid mixture which is used to perform the invention.

In case the parental nucleic acid is not naturally present in said mixture, either its denaturation temperature is known or it is determined on a control sample of said parental nucleic acid or said parental nucleic acid is added as a control in the assayed mixture, for said determination. This control may be provided as a vector, especially a plasmid, carrying the cloned parental nucleic acid or a suitable fragment thereof.

According to a particular embodiment, the differential amplification is carried out in a denaturation temperature gradient which enables in a first step, the determination of the minimum denaturation temperature for the parental nucleic acid.

According to a particular embodiment, the method involves a temperature gradient for differential amplification which gradient is within the range of 1 to 15° C., especially 1 to 10° C. from a determined denaturation temperature in order to determine the minimum denaturation temperature of the parental nucleic acid.

The method of the invention is especially performed in such a way that polymerization is carried out at a constant temperature equal to the minimum denaturation gradient temperature of the GC-rich nucleic acid and/or final elongation step is carried out at the same temperature.

The step of standard amplification may be performed as a nested PCR but not necessarily.

Primers suitable for the various PCR reactions are designed according to well known parameters for the skilled person. Some of these parameters are adapted to the particular nudeic acid to be amplified, as disclosed in the present application, especially in the examples.

Primers may be the same or may be different for the standard amplification and conversion amplification reactions on the one hand and for the differential amplification on the other hand.

In a particular embodiment of the invention, the primers used for PCR in differential amplification, are devoid of mutated nucleobases at their 3' end, with respect to the complementary sequence in the parental nucleic acid.

In a particular embodiment of the method of the invention, the primers used for PCR in differential amplification, are devoid of A and T nucleobases in the 1 to 6 nucleotides of their 3' end.

In a particular embodiment, the targeted mutant nucleic acid to be enriched in the mixture of nucleic acids is a fragment of a gene of interest, which fragment is sensitive to mutation, especially to hypermutation.

Especially, the targeted GC-rich nucleic acid to be enriched is a fragment of a gene of interest containing polymorphism(s) and the region containing said polymorphism(s) is amplified.

The method of the invention may be carried out to detect GC-rich nucleic acid through amplification, the GC-rich nudeic acid to be enriched by amplification originating from a pathogenic organism or from a gene associated with a pathogenic condition in a host especially with a human gene disorder or a tumor, or a cancer.

The pathogenic organism may be a virus or a bacteria.

The virus may be an attenuated strain and especially may be a vaccine strain.

According to a particular embodiment, the virus is a RNA virus or a DNA virus, especially it is a retrovirus or a negative RNA virus, either a segmented or a non segmented negative RNA virus, especially a mononegavirale such as a paramyxoviridae, including the measles virus (MV), or a Rift Valley Fever virus (RVFV).

According to another embodiment, the gene associated with a pathogenic condition in a host is related to a tumor state.

According to a particular embodiment of the invention, the CG-rich nucleic acid variant is a small deletion mutant of the parental nucleic acid, especially, the deletion comprises 1 or 2 bp.

In a particular embodiment the method is carried out on a nudeic acid mixture wherein the nucleic acid mixture contains the parental nudeic acid and more than one A→G mutant nucleic acid of the parental nucleic acid, wherein each mutant nucleic acid is selectively amplified compared to amplification of the parental nucleic acid.

The methods of the invention may comprise a step wherein the products of the differential PCR are detected by gel electrophoresis in agarose or acrylamide gel, capillary electrophoresis, or chromatography.

Especially, the products of the differential PCR are detected by gel filtration or ion-exchange chromatography.

According to another embodiment, the products of the PCR are identified by relative location in the gel.

In a particular embodiment, the GC-rich nucleic acid is a hypermutated variant of the parental nucleic acid in the nucleic acid mixture and the denaturing temperature is about 1 to about 3° C. lower than $T_p$ (denaturation temperature for the parental strain).

The method of the invention encompasses one embodiment wherein the GC-rich nucleic acid variant is a A→G, or a A→C mutant of the parental nucleic acid, which pairs with a fully complementary nucleic acid sequence.

According to an embodiment, the GC-rich nucleic acid variant is a T→C or T→G mutant of the parental nucleic acid, which pairs with a fully complementary nucleic acid sequence.

The method of the invention may be used for characterizing the origin of parental DNA or for detecting mutations characteristic of human gene disorders.

According to another embodiment, the method is used for detecting a A→G mutant strain of HIV (A→G hypermutants) that is resistant to antiretroviral drug.

According to another embodiment, the method is used for detecting a neurovirulent vaccine-derived poliovirus isolates that cause vaccine-associated paralytic poliomyelitis.

According to another embodiment, the parental and mutant nucleic acids are from measles virus.

The i3DPCR method according to the invention is well adapted to selectively amplifying such viral hypermutants. The viral paradigm concerns measles virus hypermutants. However, to much lower degrees, A→G hypermutants have been described for other negative RNA viruses, either segmented or non-segmented negative RNA viruses, especially paramyxoviridae such as Measles virus or other mononegavirale Rhabdoviridae such as vesicular stomatitis virus or other RNA viruses and for example parainfluenza virus or respiratory syncytial virus; it has also been observed for some retroviruses, especially lentiviruses, including HIV. Thus, the method of the invention is useful in basic research involving these and other diseases.

The i3DPCR method allows differential amplification of DNA segments differing by one to many AT→GC transitions. As the degree of substitution directly impacts the melting temperature of the DNA, the lower the denaturation temperature the more substituted the genomes amplified. As different loci may have widely different base compositions the conditions can be optimized for each segment.

Although the i3DPCR method allows differential amplification, it is not quantitative per se. However, coupled to limiting dilution of input DNA, it is possible to quantitate the fraction of GC rich genomes within a sample. Alternatively, Taqman PCR can be performed at 95° C. and the selective temperature to determine the copy number per sample. The ratio of the two values can give the relative concentration of GC-rich alleles with respect to the total concentration of all alleles.

The i3DPCR method encompasses variants that use modified bases that can influence slightly the melting temperature of DNA. For example 5-bromodUTP or dUTP can be used to replace dTTP. The differences may be small. Accordingly, use of any one of these modified bases will enhance the discrimination between the parental sequence and GC-rich nudeic acid, especially GC-rich mutant or GC-rich allele.

Equally, the i3DPCR methods also cover the use of non-standard PCR buffer conditions, particularly the use of certain salts and salt concentrations and the use of organic molecules. It is well known that the denaturation temperature can be influenced by the nature of the ion and ionic strength, for example, tetraethylammonium chloride (Muraoka et al., 1980), and the use of small organic molecules, such as methanol or polyethylene glycol, to cite just two (Muraoka et al., 1980, Votavova et al., 1986).

If random PCR is performed using a low denaturation temperature, i3DPCR can amplify GC-rich DNA from genomes. G:C rich DNA is usually synonymous with coding regions and can help in identifying genes within genomes.

More importantly, and like 3DPCR, i3DPCR can be used to identify single point mutations in a small window. Already 3DPCR has been used to identify a single G→A base change in a small locus of between 60-80 base pairs (bp). Similarly, i3PCR can identify a single A→G or T→C mutation in a small locus of 60-80 bp. Hence, the i3DPCR method can be used to identify alleles with G/C rich point mutations within a mass of normal A:T alleles. The obvious example is to look for mutations characteristic of a pre-tumoral cell.

Together 3DPCR and i3DPCR can pick up 85% of all mutations characteristic of human gene disorders or p53 inactivating lesions (Krawczak et al., 1995, Li et al., 1984). The 15% of remaining mutations concern G⇌C and A⇌T transversions. While the number of base pairs is not altered by the mutations, it is possible that stacking energies will be affected, which could lead to a change in melting temperature. If so, then 3DPCR and i3DPCR can be used to identify these mutations too.

This invention will be described in greater detail in the following Examples.

Example 1

The human immunodeficiency virus (HIV) Vif protein intercepts the host-cell proteins APOBEC3F and APOBEC3G, preventing their incorporation into budding virions (Harris et al., 2003; Wiegand et al., 2004; Zheng et al., 2004). The resulting Vif/APOBEC3 complexes are shunted to the proteasome for degradation (Sheehy et al., 2003; Yu et al., 2003). Of the seven APOBEC3 genes on human chromosome 22, at least five are transcribed (Jarmuz et al., 2002; http://genecards.bcgsc.bc.ca). They belong to a group of cytidine deaminases; the prototype of these is APOBEC1, which specifically edits the apolipoprotein B mRNA in the environment of the intestine (Teng et al., 1993). Although mRNA-editing functions have not yet been ascribed to any APOBEC3 molecule, APOBEC3C, -3F and -3G are able to extensively deaminate single-stranded DNA (Harris et al., 2003; Lecossier et al., 2003; Suspène et al., 2004; Wiegand et al., 2004; Yu et al., 2004).

In the singular context of a HIV Δvif virus, only APOBEC3F and -3G appear to be packaged into the virion (Harris et al., 2003; Bishop et al., 2004; Liddament et al., 2004; Wiegand et al., 2004; Zheng et al., 2004). It is of note that APOBEC3F and -3G are packaged during budding from the donor cell and do not enter the replication complex of an incoming virion. Consequently, as soon as minus-strand viral cDNA is synthesized in the next round of infection, the numerous multiple C residues are deaminated, yielding U. Following plus-strand DNA synthesis, the U residues are copied into A, giving rise to so-called G→A hypermutants, by reference to the viral plus strand (Pathak & Temin, 1990; Vartanian et al., 1991).

As G→A hypermutants are associated with a lethal phenotype, the absence of vif, their detection in a natural setting is, not surprisingly, highly variable and their frequency is often low. However, as GRA hypermutants frequently exhibit 20-60% of G residues substituted by A, their base composition is shifted considerably from that of the parental sequence. Hence, there is a need for a method that allows amplification of AT-rich variants and not the parental sequence.

From previous work on HIV GRA hypermutation, a large collection of molecular clones was available, corresponding to the V1V2 region of the HIV-1 envelope gene, that differed uniquely in the number of G→A transitions. A smaller region within this fragment was amplified by using Taq polymerase and degenerate primers that were derivatives of the standard SK122/SK123 pair (Goodenow et al., 1989), to result in better amplification of hypermutated genomes. Their sequences were: SK122intD, 5'-AAARCCTAAARCCA TRTRTA [SEQ ID NO: 1]; SK123intD, 5'-TAATGTATGGGAATTG-GYTYAA [SEQ ID NO: 2]. When the PCR denaturation temperature was lowered to 83° C. (the reaction profile was 5 min at 83° C., 25 cycles of 1 min at 83° C., 30 s at 45° C. and 30 s at 72° C., followed by 10 min at 72° C.), it was possible to uniquely amplify clones harbouring at least three mutations, whilst not amplifying the parental sequence (no mutations; FIG. 1a, b).

Example 2

To confirm that amplified material was indeed hypermutated and not a PCR artefact, products were electrophoresed in agarose gel containing HA-yellow (Hanse Analytik), a pegylated bisbenzamide that interacts preferentially with the minor groove of AT-rich DNA, thus retarding migration (Abu-Daya et al., 1995; Abu-Daya & Fox, 1997; Janini et al., 2001). As can be seen in FIG. 1(c), migration of PCR products in a gel containing 1 U HA-yellow (ml agarose)$^{-1}$ was retarded progressively when moving from 0 to 18 transitions per sequence, confirming the selective amplification of G→A-hypermutated DNA at 83° C.

Example 3

It is apparent from FIG. 1(b) that product recovery correlated with the extent of hypermutation. To explore more carefully the relationship between denaturation temperature and the number of G→A transitions per clone, another series of G→A-hypermutated reference clones spanning another locus within the V1V2 region was analyzed by using Taq polymerase and a different pair of primers, RT3 and RT4 (Martinez et al., 1994). Lowering the denaturing temperature by 1° C. progressively amplified more extensively hypermutated sequences (FIG. 1d). Given the exquisite relationship between denaturation temperature and AT content of a sequence, the success of amplification may also depend on the calibration of the PCR machine and perhaps upkeep and make. Accordingly, all PCRs were performed on the same machine.

These findings show that the selective amplification of G→A hypermutants is indeed generally related to the melting temperature of the target DNA. This method of the invention is referred to as differential DNA denaturation PCR, or 3D-PCR.

Example 4

FIG. 1 also shows nested PCR material (293T/PBMC) corresponding to the same V1V2 region amplified from peripheral blood mononuclear cells (PBMCs) that had been infected with a Δvif derivative of HIV-1 pNL4.3 following transfection of 293T cells. The denaturation temperature was 83° C. The fact that this material represented differentially amplified G→A hypermutants was indicated when the 3D-PCR products were electrophoresed in a gel containing HA-yellow (FIG. 1c, 293T/PBMC). When the 3D-PCR products were cloned and sequenced, the vast majority of sequences were extensively hypermutated, harbouring between three and 18 GRA transitions compared with the reference sequence (FIG. 2). Of the 18 sites bearing G→A transitions, 15 were in the context GpA and PCR material amplified at 95° C. identified only wild-type DNA (not shown).

The surprise here is that the HIV-1Δvif virus stock was made by using the 293T cell line, which is widely used as not only can it be transfected easily, but also it is considered not to express APOBEC3 molecules. From what is known of the mechanism of G→A hypermutation, the simplest explanation is that the 293T cell line had become clonally heterogeneous, so that APOBEC3F [preference for 5'TpC dinucleotide, GpA on viral plus strand (Harris et al., 2003; Liddament et al., 2004; Wiegand et al., 2004; Zheng et al., 2004)] as opposed to APOBEC3G [(5'CpC preference, or GpG on plus strand (Harris et al., 2003; Lecossier et al., 2003; Suspène et al., 2004)] was being expressed in a subset of cells. Presumably 3D-PCR was picking up DNA from viruses produced by this subset.

Example 5

Poliovirus VP1 PCR products from ten patients with post-vaccinal acute flaccid paralysis (Balanant et al., 1991) were examined. A smaller 480 bp nested segment was targeted and the denaturation conditions were investigated by using the primer pair UG1/UC1 (Guillot et al., 2000). Calibration using cloned DNA showed that the reference Sabin 1 sequence was amplified by using denaturation temperatures from 95 to 91° C., but not from 90 to 80° C. Sabin 2 and 3 targets were subtly different from Sabin 1 in that they could not be amplified below 92° C. The higher denaturation temperature used here compared with the HIV-1 locus described earlier is explained by the higher GC content of the target (48%, compared with 34% for HIV-1). Among the ten samples, only one yielded a strong signal by 3D-PCR, with the following reaction profile: 5 min at 90° C., 25 cycles of 1 min at 90° C., 30 s at 45° C. and 30 s at 72° C., followed by 10 min at 72° C. When cloned and sequenced, a series of AT-enriched sequences was obtained, with substitutions mapping particularly to VP1 residues 560-728 in the alignment of enteroviral polyproteins (www.iah.bbsrc.ac.uk/virus/picornaviridae/SequenceDatabase/alignments/entero_pep.txt). The sequences carried between one and six substitutions per segment. Of the 34 distinct substitutions, 28 were non-synonymous (including two nonsense), which is typical of variation within a quasispecies that has not undergone purifying selection. All but one substitution yielded genomes that were enriched in A and T. Amplification, cloning and sequencing of PCR material obtained at 95° C. revealed 17 clones that harboured only two substitutions in the locus shown in FIG. 3 (data not shown). Hence, it can be concluded that 3D-PCR was indeed amplifying the AT-rich end of the poliovirus mutant spectrum. As only one sample could be amplified differentially, the AT-rich variants presumably represent an unusually broad mutant spectrum and have nothing to do with the post-vaccination syndrome.

Example 6

Figure 4:
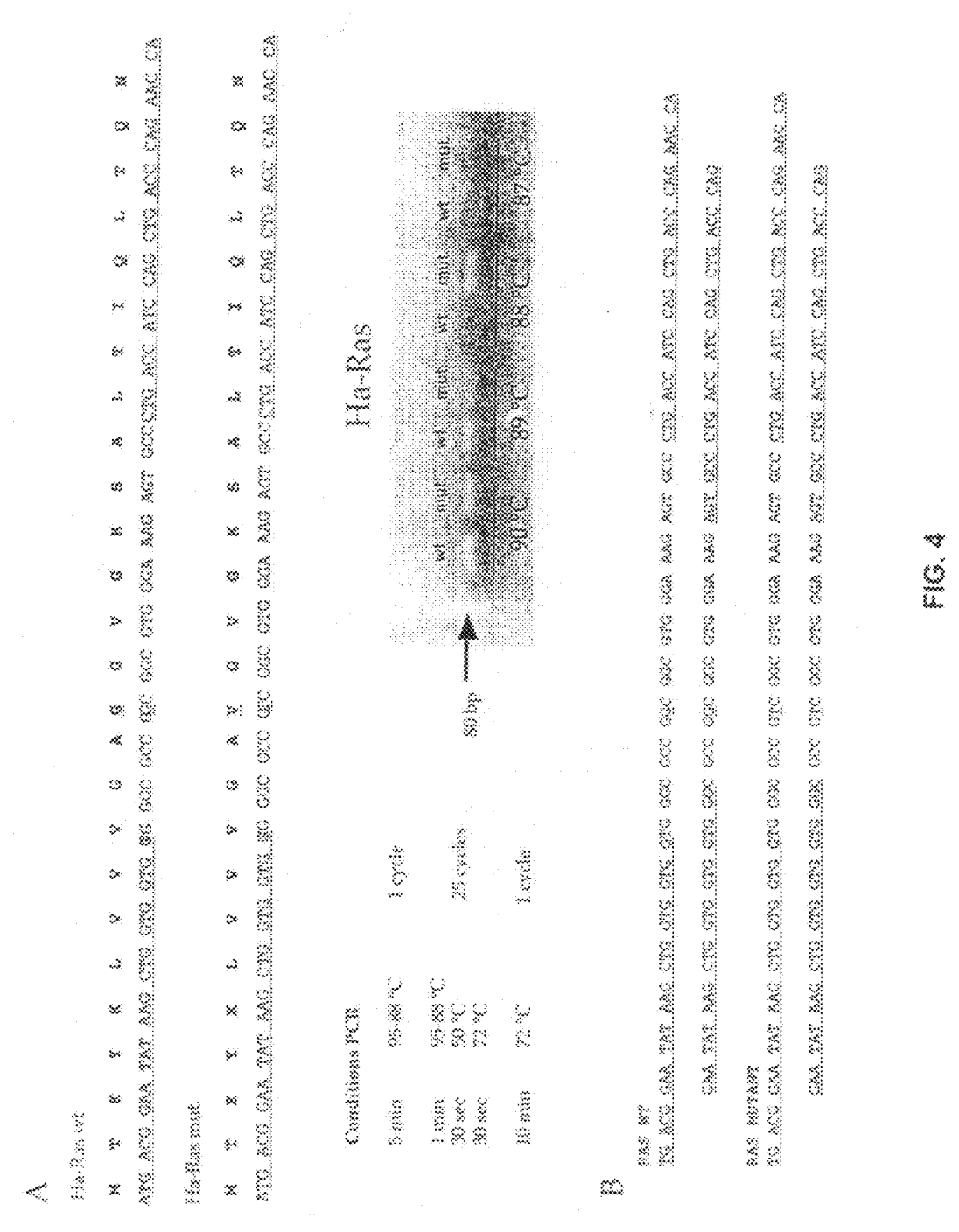

The length of the window affects the ability to discriminate between alleles differing in GC content. The longer the DNA segment the poorer the discrimination. The inverse is true to the point that an attempt was made to identify a single point mutation in a small window of as little as 30 bases. The case chosen was the p21 ras gene and the "famous" mutation in codon 12 that transforms the gene into an oncogene. The sequences of the two alleles are shown in FIG. 4A. The PCR primers are underlined as is the single G residue in the wild type sequence that is mutated to T in the oncogene. The "window" between the two primers is 29 bp.

Under standard PCR conditions, it is clear that the wild type allele was amplified at temperatures equal to and greater than 89° C. By contrast, the mutant allele could be amplified at temperatures equal to and greater than 88° C. Hence, it is indeed possible to selectively amplify alleles on the basis of a single GC→AT substitution.

The impact of amplifying across an even smaller window of 19 bp was explored. The primers are shown in FIG. 4B.

Again using standard PCR conditions, it was possible to distinguish the mutant and wt alleles. As expected for a smaller DNA fragment (69 bp compared to 79 bp), the denaturation temperatures were lower. At 86.2° C., only the mutant allele could be identified, whereas at 87.3° C., both the mutant and wild type alleles were amplified (not shown). Once again approximately one degree is sufficient to allow differential amplification.

Although technically feasible in terms of PCR, going below 69 bp may prove inconvenient for analysis by agarose gel electrophoresis as it becomes increasingly difficult to distinguish the band from that of primer-dimers. However, acrylamide gel electrophoresis, which is somewhat less convenient, is capable of distinguishing between smaller bands.

In summary, the methods of the invention, namely, 3D-PCR can be used to differentially amplify AT-enriched genomes compared with the parental genome. Although retroviral hypermutants are preferred targets for 3D-PCR, it can be applied to any sample in which there is a mutant or mutant spectrum.

3D-PCR allows differential amplification of genomes that differ by just a few GC→AT transitions. As the degree of substitution directly affects the melting temperature of the DNA, the lower the denaturation temperature, the more substituted the genomes that are amplified. As different loci may have widely different base compositions, the conditions can be optimized for each segment. Although the method allows differential amplification, it is not quantitative per se. However, coupled to limiting dilution of input DNA, it is possible to quantify the fraction of AT-rich genomes within a sample. 3D-PCR can be used to amplify AT-rich bacterial 16S rDNA sequences within a heterogeneous natural sample, neo-deaminated immunoglobulin V regions, or promoter regions that have undergone extensive 5-MeC deamination following extensive methylation.

In the precise setting of HIV, 3D-PCR has shown that one cell line that is used widely to support the replication of Δvif genomes is probably clonally heterogeneous, meaning that there is a background G→A-hypermutated signal in any sample. The ability to discriminate AT-rich variants over background indicates that this technique can be employed in a variety of applications to biological questions.

Example 7

Detection of CG Hypermutated Polynucleotides or CG Rich Alleles in Viral Genomes
Introduction It is a truism that a GC base pair has three hydrogen bonds while AT has two. In fact, Watson & Crick didn't quite see it that way back in 1953 (1, 2). It was Pauling and Corey who demonstrated the validity of the third hydrogen bond in the GC pair in 1956 (3). The third hydrogen bond helps understand why GC rich DNA melts at higher temperatures than does AT rich DNA. Indeed, when performing PCR on GC rich segments the denaturation temperature is sometimes increased to ensure complete DNA melting (4).

Generally speaking, the denaturation temperature has not been considered as a variable in PCR. Recently, lower denaturation temperatures were exploited to selectively amplify so-called G→A hypermutants of the human immunodeficiency virus (HIV) (5). They arise from genetic editing of nascent viral cDNA by two host cell cytidine deaminases of the APOBEC3 family (6-11). Deamination of numerous cytidine (C) residues on the viral minus strand yields multiple uracil (U) residues, which are read as a thymidine (T). With respect to the viral plus strand as reference, these show up as genomes with numerous G→A transitions giving rise to the term G→A hypermutants (12, 13). Temperature differences as small as 1-2° C. were enough to allow differential amplification of A rich hypermutants in the presence of as much as $10^4$ fold excess of wild type, or reference genomes (14, 15). The method was referred to as differential DNA denaturation PCR, or 3D-PCR for short (5). Obviously the inverse is not possible, that is selective amplification of GC rich alleles with respect to a reference clone, because such alleles would melt at even higher temperatures.

This not a moot point in virology for there are examples of A→G hypermutated RNA viral genomes, the paradigm being measles virus (MV). Such genomes have been identified in autopsy samples from cases of MV-associated subacute sclerosing panecephalitis and inclusion body encephalitis (16). They arise from deamination of numerous adenosine residues in the context of double stranded RNA (dsRNA) by adenosine deaminases of the ADAR family (for review see (17)). Editing of adenosine yields inosine (I). As I hydrogen bonds essentially as guanosine (G), edited RNA sequences are recovered as G rich alleles. The extent of editing may vary from a few bases to up to 50% of potential target adenosine residues (18, 19).

Of the two ADAR1 gene transcripts ADAR-1L and -1S, only the former can be induced by interferon α/β and γ (20). Despite this, the number of examples of ADAR edited RNA viral sequences has remained little more than a handful, being confined mainly to negative stranded viruses such as vesicular stomatitis virus, respiratory syncytial virus and paramyxovirus (19, 21, 22) the signal exception being measles virus in vivo. The genome of the hepatitis D satellite virus may also be edited by ADAR-1L (23). Nonetheless, it is not too clear what the impact of ADAR-1L editing has on RNA viral replication (24).

Given this, it would be useful to have a PCR based method to allow selective amplification of GC-rich alleles. In view of the 3:2 hydrogen bonding rule for GC and AT base pairs, differential denaturation of target DNA would appear to be out of the question. Noting that inosine base pairs with cytidine through two hydrogen bonds rather than the three typical for a GC base pair (FIG. 6), the inventors have now conceived that this could participate to the design of an appropriate method for the selective amplification of GC-rich alleles.

Modified bases are often encountered in DNA bacteriophage genomes, usually as a means to avoid host restriction enzymes (25). Invariably modifications involve cytidine or thymidine, for example 5-hydroxymethyl cytidine in phage T4 DNA. There is however, just one example of a modified purine, 2,6-aminoadenosine. It is found in the cyanophage S-2L DNA genome where adenosine is totally substituted by 2,6-diaminopurine (26), or "D", and has the singular feature of base pairing with thymidine (T) via three hydrogen bonds (FIG. 6). As dITP and dDTP are commercially available and are substrates for some thermostable DNA polymerases (27), they may thus be involved in a PCR based method allowing selective amplification of GC-rich alleles. Such a method has been designed, encompassing a combination of differential denaturation PCR using the modified bases, i.e., dITP and dDTP.

Results

Figure 7:
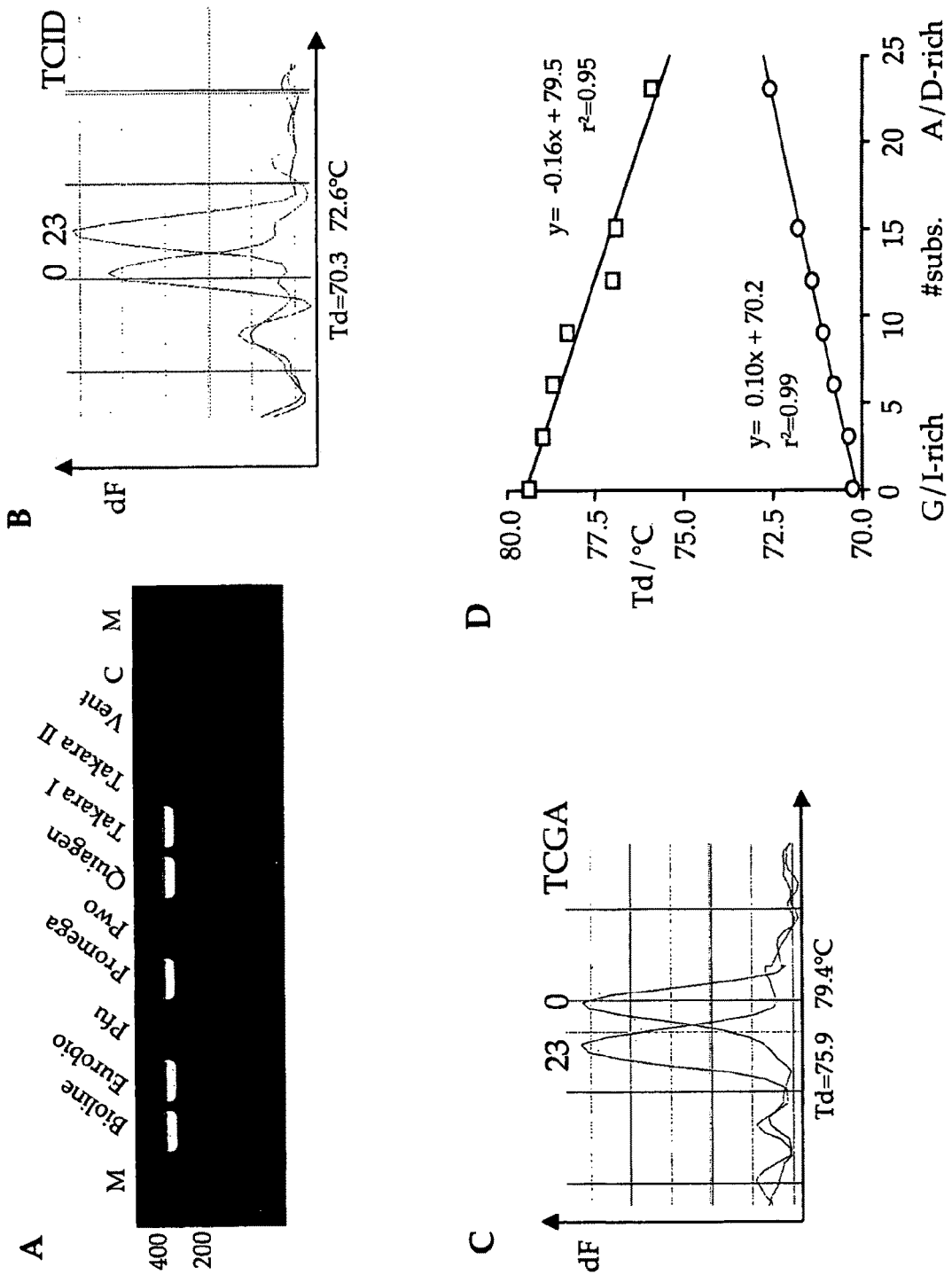
FIG. 7. PCR using dITP and dDTP substrates and denaturation profiles. A) Five of 8 commercially available thermostable polymerases can efficiently incorporate dITP and dDTP into DNA. dNTP concentrations were 200 μM throughout, [$Mg^{2+}$]=2.5 mM, Td=95° C. C=negative polymerase control, M=markers in bps. The Bioline, Eurobio, Promega, Quiagen and Takara enzymes are all variants of Taq polymerase. Takara I and II refers to two buffers supplied by the manufacturer. B) SYBR Green melting profiles for TCGA DNA corresponding to the HIV-1 V1V2 region. The reference is marked "0" while "23" denotes the clone differing uniquely by 23 G→A transitions. Midpoint Tds are given below the x-axis. C) SYBR Green melting profiles for TCID DNA corresponding to the HIV-1 V1V2 region. Midpoint Tds are given below the x-axis. D) Linear correlation between midpoint Td and G/I or ND composition of 7 HIV-1 clones whose sequences are given in FIG. 10.

A wide variety of thermostable DNA polymerases were first screened for their ability to amplify DNA using dTTP, dCTP, dITP and dDTP. Using a standard buffer and a 95° C. denaturation temperature, ⅝ thermostable polymerases resulted in reasonable product recovery after 30 cycles using an extended elongation time of 1 minute (FIG. 7A). All five were commercial variants of Taq polymerase. At 20 cycles the Bioline enzyme gave better product yield and was therefore used in all subsequent work (not shown). However, product recovery was inferior compared to amplification using standard dNTPs. Increasing the concentration of dITP and dDTP to 300 μM did not increase product yield. Although inosine base pairs essentially as guanine, it can form base pairs with T and A, hence the use of dITP in PCR is somewhat mutagenic (28). In an attempt to favour dC:dITP pairing the concentration of dCTP was increased from 200 to 300 μM while the dTTP was lowered to 100 μM and the fidelity compared to that resulting from amplification using equimolar 200 μM dNTPs. As no change in PCR fidelity was found ($4.1\ 10^{-3}$ vs $3.9\ 10^{-3}$ per base), all subsequent amplifications were performed using equimolar dNTPs.

The denaturation properties of PCR DNA containing the two modified bases (TCID DNA) was established for a series of seven 262 bp molecular clones that differed only by up to 23 G/A transitions distributed across the locus (FIG. 10). As can be seen from SYBR Green melting profiles, midpoint denaturation temperatures (Td) of 70.3 and 72.6° C. were obtained for TCID DNA the G/I and A/D-rich clones respectively, as expected from the change in hydrogen bonding patterns (FIG. 7B). For standard PCR products (i.e. TCGA DNA) the inverse prevailed, i.e. the A-rich allele was denatured at a lower temperature, Td=75.9° C., than the G-rich allele (79.4° C., FIG. 7C). The midpoint Tds of the seven molecular clones varied linearly with G/I or A/D content (FIG. 2D). The temperature sensitivity of TCID DNA to G/I content was only ~60% that of TCGA DNA. That the two gradients do not cross is in keeping with previous observations that total dI substitution lowers the Td of DNA more than dD substitution increases it (27).

Recovery of In Vitro Hyperedited MV Sequences

We sought to validate the method using MV samples grown in the interferon sensitive cell line MRC-5. As a control Vero cells were used which are defective for interferon-β production. The attenuated MV Schwartz strain was used because it is a good inducer of interferon. Two days post-infection supernatant and cell pellets were collected and total RNA extracted. cDNA was converted into PCR products, a fraction of which was converted into TCID PCR products using a 95° C. denaturation temperature. Selective TCID amplification was then applied to the TCID DNA using a denaturation gradient of 63-72° C. As can be seen from FIG. 3A the minimum temperature at which MV genomes could be amplified from Vero cells was 67.4° C. By contrast MV specific products could be amplified from the MRC-5 cells down to 65° C. TCID products amplified at the lowest Td were used for molecular cloning into TOPO plasmids. Probably in view of the unusual bases, transformation of standard bacteria with cloned TCID products not only gave very low efficiencies, but also was invariably accompanied by large deletions within the MV sequences. To overcome this, a fraction of TCID PCR products was converted into standard DNA by 10 cycles of PCR using normal dNTPs and then cloned. As controls, DNA amplified from reactions using a Td=95° C. were also cloned and sequenced.

As can be seen from FIG. 8B the MV genomes selectively amplified from MRC-5 cells (Td=65° C.) were littered with A→G transitions. Indeed, up to 83.3% of A residues could be edited (m=70%, range 3.3-83.3%). By contrast, those amplified from MV-infected Vero cells at the lowest possible temperature (Td=67.4° C.) were typical of quasispecies variation of an RNA virus. A slight AU⇌GC skew in the substitution matrix (FIG. 8C) is understandable given the selective PCR protocol. MV sequences amplified under standard PCR conditions (Td=95° C., normal dNTPs) showed balanced mutation matrices (FIG. 8C). This indicates that the highly edited sequences from the MRC-5 cell line must represent a subset, and that the selective PCR protocol was indeed capable of recovering GC rich alleles. To ascertain their frequency, the initial TCID products were serially diluted and standard and selective PCR performed. The signal from standard PCR titrated out 100-fold further than selective PCR indicating that the highly edited genomes were present in the sample at ~1% (data not shown).

As can be seen from the substitution matrix for MRC-5 derived MV sequences (Td=65° C., FIG. 8C), A→G transitions dominated consistent with editing of the negative stranded viral genome. However, U→C transitions were slightly more numerous than C→U. Inspection of the sequences revealed 2/22 sequences, one of which harboured both A→G+U→C transitions, while the other bore uniquely U→C transitions (FIG. 8D). The latter is consistent with ADAR editing of the MV anti-genome while the former reflects editing of both the genome and anti-genome, although the order of editing cannot be established. As A→G hypermutants could be found in viral supernatants from MV-infected MRC-5 cells, this suggests that either edited MV genomes can be packaged or that RNA editing can occur post packaging (FIG. 11).

We refer to this novel method as inverse differential DNA denaturation PCR, or 3DI-PCR, to distinguish it from 3D-PCR that allows amplification of AT-rich DNA (5).

Editing of a Segmented Virus RNA

Given the relative dearth of edited genomes, MV and HDV apart, we decided to study another (−) RNA virus, Rift Valley fever virus (RVFV), a segmented negative stranded RNA virus, for which there are no reports of ADAR edited RVFV genomes. In short, can 3DI-PCR make novel findings? RVFV clone 13 (29) is a highly immunogenic yet attenuated strain that encodes a 549 bp in frame deletion within the NSs gene. As the vestigial NSs protein has lost its ability to antagonize interferon production, clone 13 is a good inducer of interferon, unlike virulent strains (29). While clone 13 grew well on Vero cells, viral titres were 100 fold lower on MRC-5 cells.

Figure 12A:
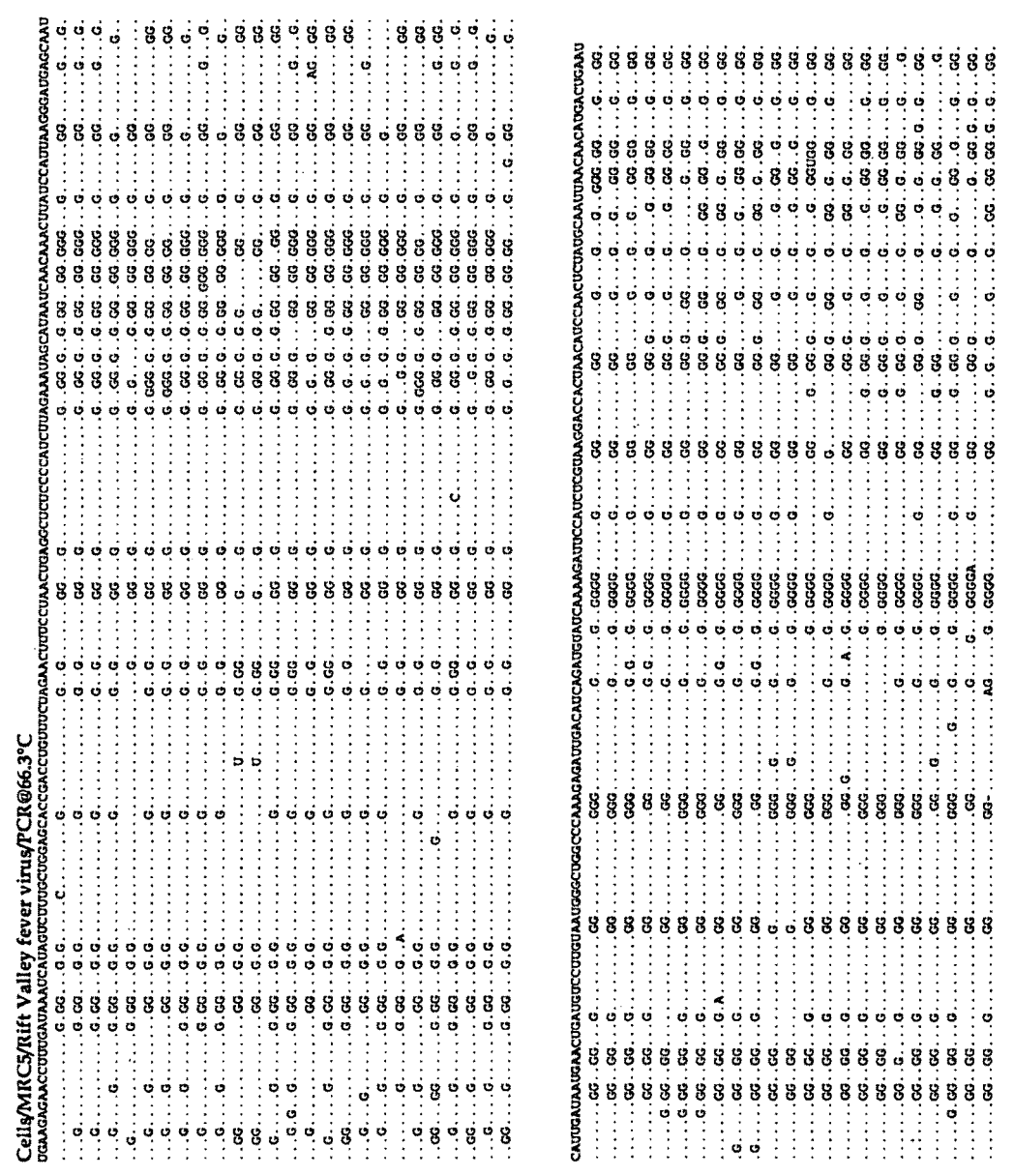
Figure 12B:
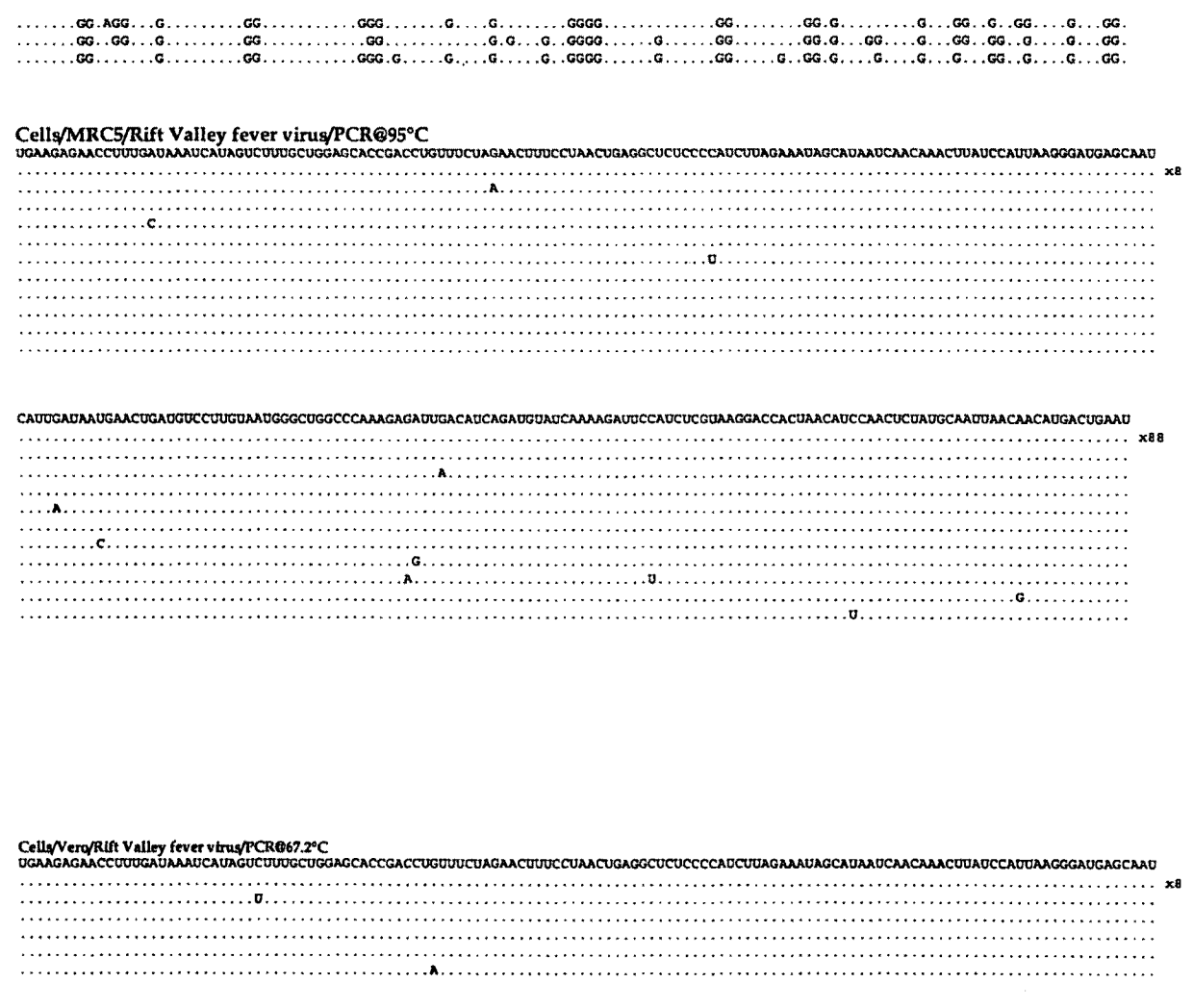
Figure 12C:
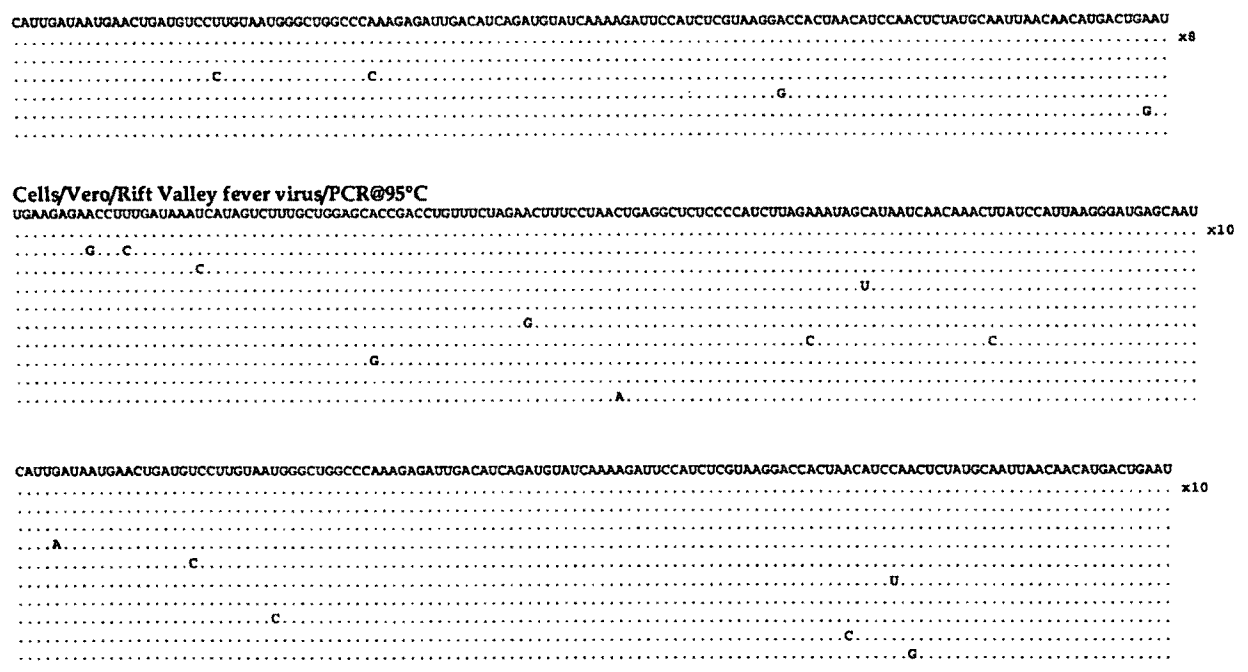
Figure 9:
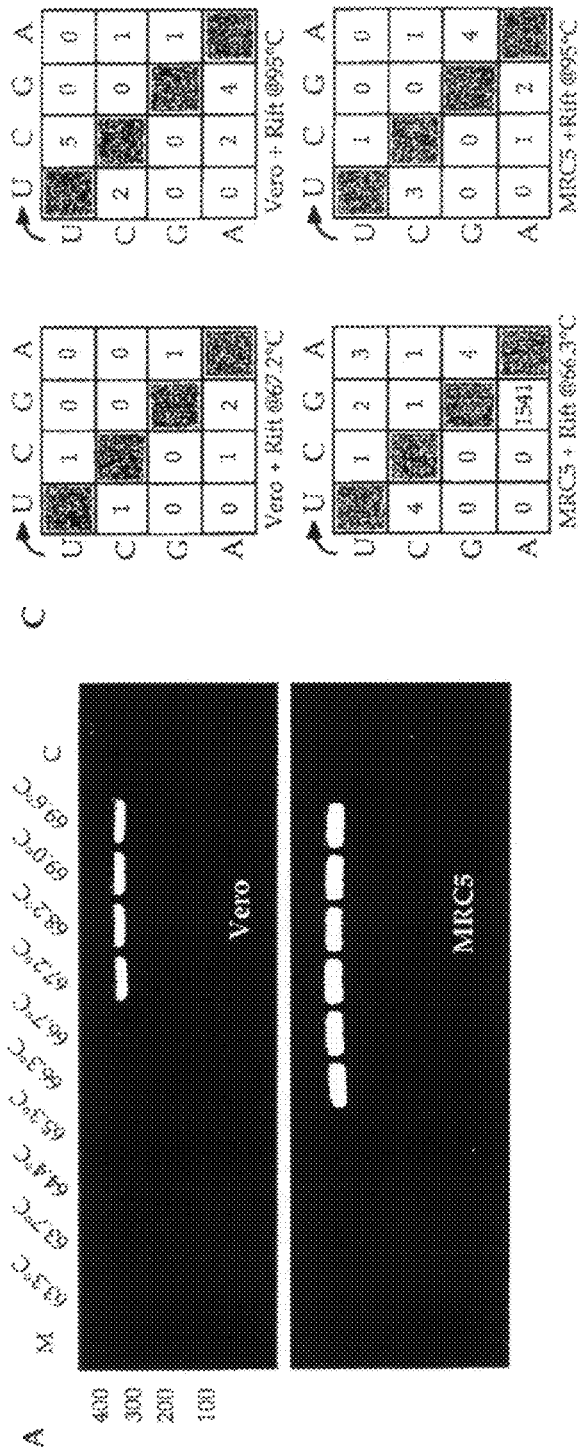
FIG. 9. Massive adenosine deamination of Rift Valley fever virus genomes. A) Agarose gel of TCID DNA amplified from RVFV infected Vero and MRC-5 cells. The PCR products amplified from the latter between 66.3-66.7° C. are indicative of genomes enriched in GC. C, negative control; M molecular weight markers. B) RVFV sequences derived from amplification at the lowest denaturation temperature (66.3° C.). Sequences are aligned to the reference MV sequence, only differences being shown. The monotonous A→G transitions are typical of ADAR editing. Complete sequence sets are given in FIG. 12 C) Mutation matrices for the sequence sets. The number of sequences per matrix is, starting top left and going clockwise n=6, 10, 11 and 26. The symmetry of the mutation matrices at 95° C. amplification controls is typical of a viral quasispecies.
Figure 13:
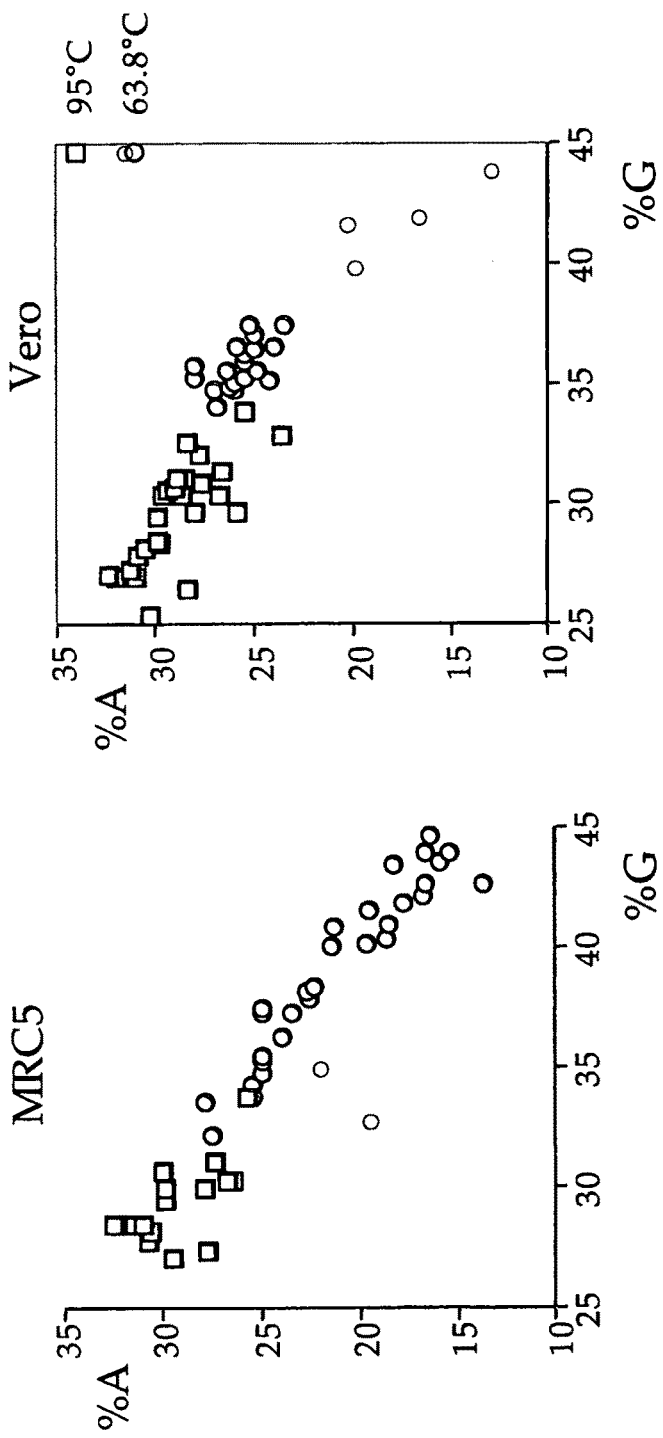
FIG. 13 shows the base composition of the amplified Alu sequences embedded in the host cell mRNA sequences.

Clone 13 was cultured on both cell lines for 3 days and total cellular RNA recovered. Using primers specific for a 257 bp fragment from the L gene, 3D1-PCR could recover RVFV genomes at a lower temperature from the restrictive MRC-5 culture compared to the permissive Vero cell culture, 66.3° C. compared to 67.2° C. (FIG. 9A). Cloning and sequencing of the PCR products revealed extensive A→G editing of viral RNA from the MRC-5 culture and nothing more than a quasispecies variation from the Vero cells (FIG. 9B, C). Although a handful of hyperedited sequences are shown, all 26 clones derived from the MRC-5 infection were distinct and harboured between 63-77% of edited adenosine targets. Thus hyperediting of RVFV RNA in MRC-5 can be just as extensive as for MV in the same cell line. When analyzed by standard PCR (Td=95° C., normal dNTPs) the mutation matrices were balanced, indicating that the highly edited RVFV genomes identified represent a minority (FIG. 9C). Complete RVFV sequence sets can be found in FIG. 12.

Variations on a Selective Amplification Theme

As can be seen from FIG. 7D, 3DI-PCR is less sensitive to differences in GC content than is 3D-PCR. In an attempt to manipulate the denaturation sensitivity of TCID DNA, range of small organic molecules that bind to DNA via the minor groove, i.e. Hoechst bisbenzmide dye H33258, modified bases such as dUTP, 5-MedCTP and 7-deazadGTP, monovalent ($K^+$) and divalent cations ($Mn^{2+}$) were explored. Although the absolute Tds varied, none of the reagents had any significant impact on the denaturation temperature/base composition relationship of the seven standards (not shown). Finally, GC-intercalating reagents such as DAPI, which lowers the Td of DNA were of no use for they blocked amplification, even at very low concentrations (10 nM). In short, while the overall Td can be manipulated the denaturation temperature/base composition relationship of TCID DNA is relatively refractory to manipulation.

Discussion

Differential DNA denaturation PCR exploits the intrinsic stability of GC base pairs arising from an additional hydrogen bond, and allows selective amplification of AT-rich DNA. By using modified bases the 3:2 rule can be inverted, allowing selective amplification of GC-rich alleles. A range of commercially available Taq polymerases was able to undertake incorporation of the two modified bases, although products yields are somewhat less than when standard dNTPs are used. The temperature/GC content coefficient for 3D- and 3DI-PCR were not equivalent, the latter being ~60% less than the former (FIG. 7D). Nonetheless, 3DI-PCR is simple and sufficiently robust to prove useful in virology. It is a trifle longer than 3D-PCR in that it requires an initial conversion of DNA into TCID DNA.

When applied to measles virus, the prototypical example of ADAR edited viral genomes, highly edited genomes were recovered from the MRC-5 culture. Not only are the MV genomes more extensively edited from cultured virus than in vivo, they are more heterogeneous (19). That such genomes were present at frequencies of ~1% in the MRC-5 culture may help explain why MV A→G hypermutants have not been described before in culture. The finding of numerous A→G hypermutants in culture of RVFV clone 13 is also novel and suggests that, as negative stranded RNA viruses are in general good inducers of interferon, similar findings could be obtained with such viruses if grown on interferon sensitive cells.

The question of the significance of an interferon induced response that generates "only" 1% hypermutated viral genomes merits comment. The MV sequence sets shown in FIG. 8B were obtained at the lowest positive Td, i.e. 65° C. While not shown here, we know that MV sequences taken from the sample Td=66.2° C. were less extensively substituted suggesting that there is a large range in the degree of editing, probably reflecting the levels of ADAR-1L expression and the numbers of deaminases packaged. If larger segments were analyzed the proportion of edited sequences would increase greatly. Hence the true number of edited MV genomes is probably much greater than 1%. As the genomic mutation rate for MV (~1.4 substitutions per cycle (30)) is close to the error threshold for RNA viruses, a little adenosine deamination should be sufficient to kill the virus (31).

While 3DI-PCR can clearly amplify hyperedited genomes what is the lower limit of editing detectable? From FIG. 7D it would appear that clones harbouring 3-4 edited sites within a 265 bp fragment can be distinguished from each other. While the vast majority of MV and RVFV genomes were extensively edited there was one MV clone bearing just 2 A→G transitions. Hence it would seem that the lower limit may be of the order of ~2 sites/265 bp. The actual limitation comes from the thermal stability of the gradient Mastercycler which is ~0.3-0.4° C. It is possible that 3DI-PCR could prove useful in analyses of ADAR edited cellular mRNAs where occasionally 3-5 bases can be edited (32, 33).

3DI-PCR is robust and simple to perform, dDTP and dITP being commercially available reagents. It is a trifle longer in that extra PCR steps are necessary to perform the selective amplification as well as to obtain reasonable cloning efficiencies. The PCR denaturation temperature has hitherto remained a constant, understandably so as the aim was to denature all DNA. With the use of modified nucleotides, PCR can now be extended to allow selective amplification of both AT- and GC-rich DNA.

Materials and Methods

Viruses.

MRC5 and Vero cells were grown in Dulbecco's modified Eagle's medium containing 5-10% fetal calf serum and antibiotics (5 U/ml penicillin and 5 µg/ml streptomycin) in the presence of 5% $CO_2$. Cell monolayers in 6-well plates were infected with live attenuated measles virus (Schwarz strain amplified on Vero cells) at a multiplicity of infection of 0.1 for Vero cells and 3 for MRC-5. Two days after infection culture medium was collected and cells were trypsinized. After clarification of cell debris, RNA was extracted. Subconfluent monolayers were infected with RVFV clone 13 at a multiplicity of infection of 0.01 pfu per cell and incubated for 3 days at 37° C.

RNA Extraction, Oligonucleotides and PCR Reagents and Cloning.

Samples including cell lysates and viral supernatants were digested in SDS/proteinase K buffer (0.1 mg/ml, Eurobio) at 56° C. for 2 h. Total nucleic acids were extracted using the MaserPure™ complete DNA and RNA purification kit (Epicentre) according to the manufacturer's procedure. Total RNA was then reverse transcribed in a final volume of 20 μl of a mixture containing 1× buffer reaction (Gibco), 300 ng of random hexamers (Pharmacia), 500 μM each standard dNTP, 10 U of MLV reverse transcriptase (Invitrogen) and 10 U RNAsin (Promega). Ten percent of the reaction was used for PCR amplification.

A fragment of the M gene of MV and of the L gene of RVFV clone 13 was amplified by a nested procedure. To increase sensitivity and specificity, a hot-start PCR was performed for both amplifications. First-round primers for MV were 5'ROUout and 3'ROUout respectively 5'GGCAGGCYGGYGCCCCAGGYCAGAG and 5'GGRRCCTCTGCGGGGTRTCGRGCGG, and maps to 3522-3903 on the Schwarz genome. The primers may also be used for PCR conversion reaction.

For the second round (i.e., selective amplification by differential PCR), primers were 5' ROUin and 3' ROUin, respectively 5'AGAYCCYGGYCYAGGCGACAGGAAGG and 5'GCRTTGCRCRCTTGGTTTGCGTTG, where Y=T/C and R=A/G. First-round primer for RVFV amplification were 5'RFout and 3'RFout respectively 5'GTCGCCAATGYCGAGGAGGCCCAYGA and 5'CTCCAGATCATCTRTCCTRRTGCTTCC, and map to 5872-6255 on the L fragment of RVFV. For the second round, primers were 5'RFin and 3'RFin respectively, 5'GATGATAGAAGAYGCCAAGAACAAYGC and 5'TGCTTCCTTCTGGTCTCTGTRGRGTTC.

Standard dNTPs were purchased from Sigma, dDTP, dITP, dUTP, 5Me-dCTP were purchased from Biolink. DAPI was from Fluka while 7-deazadGTP and the Hoechst bisbenzamide dye (H33258) were from Sigma. PCR products were purified from agarose gels and ligated into the TOPO TA cloning vector cloned and sequenced as described (5).

PCR Protocol.

Hypermutated genomes were identified by a three-step protocol. The first reaction involved a standard amplification of PCR to generate sufficient material. Conditions were: 2.5 mM $MgCl_2$, 50 mM KCl, 10 mM Tris-HCl (pH 8.3), 200 μM of dATP, dTTP, dCTP and dGTP, 100 μM each primer, and 5 U of BioTaq DNA polymerase (Bioline) in a final volume of 50 μl. The second reaction converted standard DNA to that containing the modified based D and I, referred to as TCID DNA. This is essential because if input material is TCGA DNA the Tds of GC-rich alleles are governed by the natural base pairing rule and so cannot be differentially amplified. The conditions were as above except that 200 μM each dTTP, dCTP, dDTP and dITP, 100 μM each primer and 10 U of BioTaq DNA polymerase (Bioline) were used in a final volume of 50 μl. The denaturation temperature was 95° C.

Differential amplification was performed in the third round using an Eppendorf gradient Mastercycler S programmed to generate 2-10° C. gradients in the denaturation temperature. The reaction parameters were performed by using, for example, a 8° C. denaturation gradient for 5 min, followed by 35 cycles (a 8° C. denaturation gradient for 30 s, annealing 55° C. for 30 s, and constant polymerization temperature equal to the minimum denaturation gradient temperature for 1 min) and finally 10 min at the minimum denaturation gradient temperature to finish elongation. While the magnitude of the denaturation gradient can be changed, the constant polymerization temperature is always equal to the minimum denaturation gradient temperature. The buffer conditions were 2.5 mM $MgCl_2$, 50 mM KCl, 10 mM Tris-HCl (pH8.3), 200 μM each dTTP, dCTP, dDTP and dITP, 100 μM each primer and 10 U of BioTaq DNA polymerase (Bioline) in a final volume of 50 μl.

Example 8

Detection Assay Based on Alu Sequences in mRNA of Cells

As ADAR editing concerns A residues, and yields G residues, the A and G content for each sequences can be represented on the y and x-axes respectively. Two sets of data are shown from two different cell lines. Messenger RNA derived from the MRC cell line infected by measles virus was used. In this cell line type I interferons are induced so resulting in ADAR-1L expression. The Vero cells also were infected by measles virus. However, as there is a defect in the interferon beta gene in this cell line, no type I interferons are produced.

Open squares denote the A vs. G base composition of mRNA embedded Alu sequences derived by standard PCR amplification using a 95° C. denaturation temperature. Open circles denote the A vs. G base composition of mRNA embedded Alu sequences derived by 3DI-PCR at a 63.8° C. denaturation temperature. The input cDNA material was the same for the two amplifications. As can be seen 3DI-PCR selectively amplified G rich sequences compared to classical PCR as expected given the use of the modified bases dDTP and dITP.

Once again, this provides a proof of concept, amplification of GC rich nucleic acids. However, this example is interesting in that it extends the use of the method beyond virology into the realm of cellular biology and general mRNA editing. It is to be expected that the technique can used to amplify up GC rich alleles, GC rich DNA from mixtures of bacteria/archaeabacteria or GC rich variants of somatically modified immunoglobulin V gene sequences. These are but some examples. The method applies to any GC rich sequence or variant.

Materials and Methods

Cells.

MRC5 and Vero cells were grown in Dulbecco's modified Eagle's medium containing 5-10% fetal calf serum and antibiotics (5 U/ml penicillin and 5 μg/ml streptomycin) in the presence of 5% $CO_2$. Cell monolayers in 6-well plates were infected with live attenuated measles virus (Schwarz strain grown on Vero cells) at a multiplicity of infection of 0.1 for Vero cells and 3 for MRC-5. Two days after infection culture medium was collected and cells were trypsinized. After clarification of cell debris, RNA was extracted. Subconfluent monolayers were infected with RVFV clone 13 at a multiplicity of infection of 0.01 pfu per cell and incubated for 3 days at 37° C.

RNA Extraction, Oligonucleotides and PCR Reagents and Cloning.

Samples including cell lysates and viral supernatants were digested in SDS/proteinase K buffer (0.1 mg/ml, Eurobio) at 56° C. for 2 h. Total nucleic acids were extracted using the MaserPure™ complete DNA and RNA purification kit (Epicentre) according to the manufacturer's procedure. Total RNA was then reverse transcribed in a final volume of 20 µl of a mixture containing 1× buffer reaction (Gibco), 300 ng of random hexamers (Pharmacia), 500 µM each standard dNTP, 10 U of MLV reverse transcriptase (Invitrogen) and 10 U RNAsin (Promega). The cDNA primer was Alu1 (see below). Ten percent of the reaction was used for PCR amplification.

The primers specific for the amplification of mRNA embedded Alu sequences were:

```
Alu1     5' CACGCCTGTAATCCCAGCACTTTGGG
Alu2     5' TGTCGCCCAGGCTGGAGTGCAGTGG
```

Figure 8:
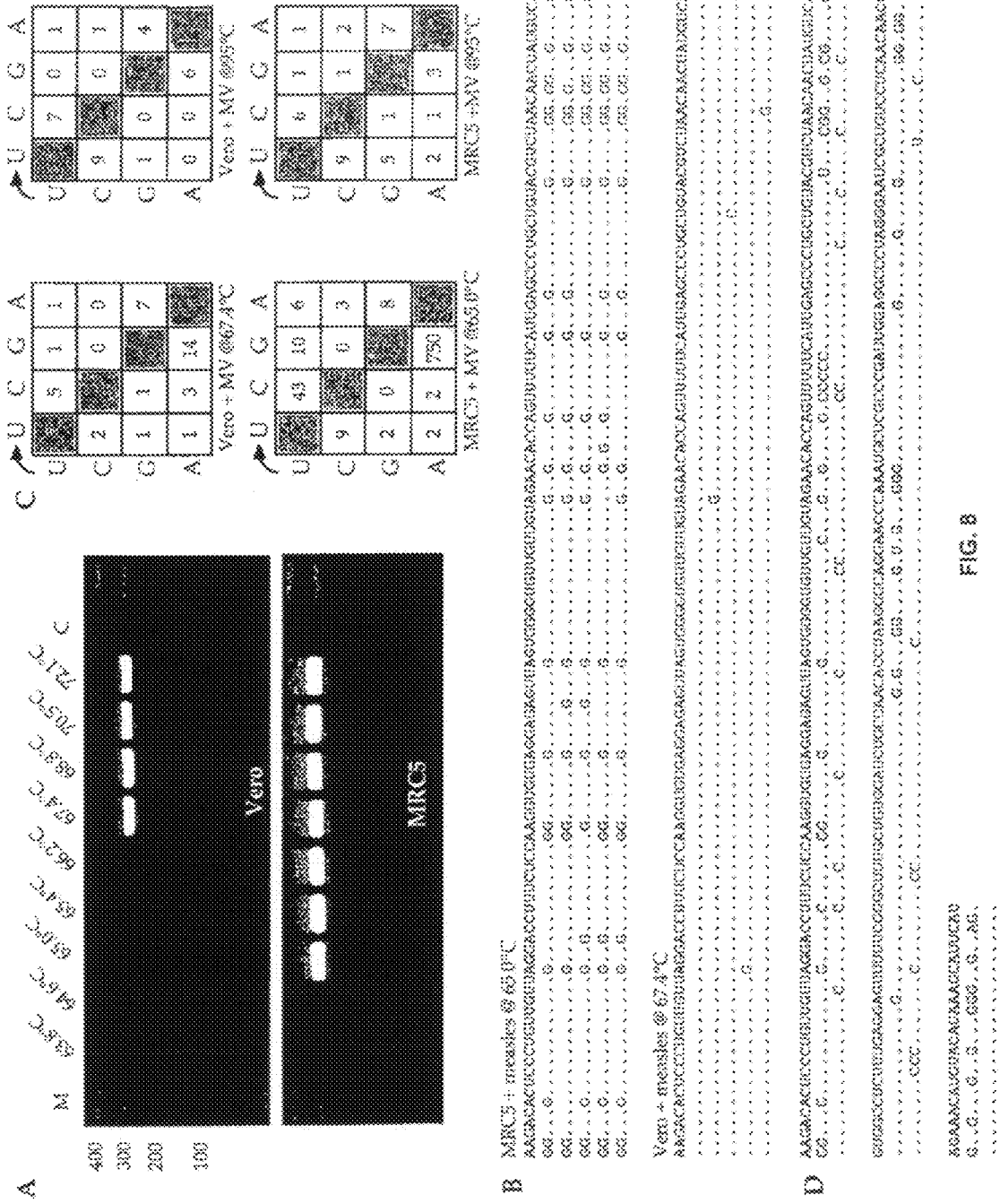
FIG. 8. 3D1-PCR amplification of ADAR edited measles virus genomes. A) Agarose gel of TCID DNA amplified from measles infected Vero and MRC-5 cells. The PCR products amplified from the latter between 65.0-66.2° C. are indicative of genomes enriched in GC. C, negative control; M molecular weight markers. B) MV sequences derived from amplification at the lowest denaturation temperature (65.0° C.). Sequences are aligned to the reference MV sequence, only differences being shown. The monotonous A→G transitions are typical of ADAR editing. Complete sequence sets are given in FIG. 11 C) Mutation matrices for the sequence sets. The number of sequences per matrix is, starting top left and going clockwise n=15, 13, 21 and 19. The symmetry of the mutation matrices at 95° C. amplification controls is typical of a viral quasispecies. A slight skew towards in Vero/MV 67.4° C. matrix from AU→GC is understandable given that 3DI-PCR amplifies GC rich sequences, and represents the GC-rich end of the mutant spectrum. D) Sequences of two C rich MV sequences compared to the reference genome. The first encodes A→G and U→C transitions and arises from editing of the viral genome and anti-genome, while the latter U→C transitions indicating editing only of the anti-genome.

They were inspired by FIG. 8 of a paper by Athanasiadis et al. (33).

Standard dNTPs were purchased from Sigma, dDTP and dITP were purchased from Biolink. PCR products were purified from agarose gels and ligated into the TOPO TA cloning vector cloned and sequenced as described (Suspene, R., et al (5).

PCR Protocol.

Hypermutated genomes were identified by a three-step protocol. The first reaction involved a standard amplification of PCR to generate sufficient material. Conditions were: 2.5 mM $MgCl_2$, 50 mM KCl, 10 mM Tris-HCl (pH 8.3), 200 µM of dATP, dTTP, dCTP and dGTP, 100 µM each primer, and 5 U of BioTaq DNA polymerase (Bioline) in a final volume of 50 µl. The second reaction converted standard DNA to that containing the modified based D and I, referred to as TCID DNA. This is essential because if input material is TCGA DNA the Tds of GC-rich alleles are governed by the natural base pairing rule and so cannot be differentially amplified. The conditions were as above except that 200 µM each dTTP, dCTP, dDTP and dITP, 100 µM each primer and 10 U of BioTaq DNA polymerase (Bioline) were used in a final volume of 50 µl. The denaturation temperature was 95° C.

Differential amplification was performed in the third round using an Eppendorf gradient Mastercyder S programmed to generate 2-10° C. gradients in the denaturation temperature. The reaction parameters were performed by using a 15° C. (75° C. to 60° C.) denaturation gradient for 5 min, followed by 35 cycles (a 15° C. (75° C. to 60° C.) denaturation gradient for 30 s, annealing 55° C. for 30 s, and constant polymerization temperature equal to the minimum denaturation gradient temperature for 1 min) and finally 10 min at the minimum denaturation gradient temperature to finish elongation. While the magnitude of the denaturation gradient can be changed, the constant polymerization temperature is always equal to the minimum denaturation gradient temperature. The buffer conditions were 2.5 mM $MgCl_2$, 50 mM KCl, 10 mM Tris-HCl (pH8.3), 200 µM each dTTP, dCTP, dDTP and dITP, 100 µM each primer and 10 U of BioTaq DNA polymerase (Bioline) in a final volume of 50 µl.

REFERENCES

The entire disclosures of each of the following publications are relied upon and incorporated by reference herein.

1. Watson, J. D. & Crick, F. H. (1953) *Nature* 171, 964-7.
2. Wain-Hobson, S. (2006) *Nature* 439, 539.
3. Corey, R. B. & Pauling, L. (1956) *Arch Biochem Biophys* 65, 164-181.
4. Smith, S. M., Markham, R. B. & Jeang, K. T. (1996) *Proc Natl Acad Sci USA* 93, 7955-7960.
5. Suspene, R., Henry, M., Guillot, S., Wain-Hobson, S. & Vartanian, J. P. (2005) *J Gen Virol* 86, 125-129.
6. Harris, R. S., Bishop, K. N., Sheehy, A. M., Craig, H. M., Petersen-Mahrt, S. K., Watt, I. N., Neuberger, M. S. & Malim, M. H. (2003) *Cell* 113, 803-809.
7. Lecossier, D., Bouchonnet, F., Clavel, F. & Hance, A. J. (2003) *Science* 300, 1112.
8. Mangeat, B., Turelli, P., Caron, G., Friedli, M., Perrin, L. & Trono, D. (2003) *Nature* 424, 99-103.
9. Mariani, R., Chen, D., Schrofelbauer, B., Navarro, F., Konig, R., Bollman, B., Munk, C., Nymark-McMahon, H. & Landau, N. R. (2003) *Cell* 114, 21-31.
10. Suspene, R., Sommer, P., Henry, M., Ferris, S., Guetard, D., Pochet, S., Chester, A., Navaratnam, N., Wain-Hobson, S. & Vartanian, J. P. (2004) *Nucleic Acids Res* 32, 2421-2429.
11. Wiegand, H. L., Doehle, B. P., Bogerd, H. P. & Cullen, B. R. (2004) *Embo J* 23, 2451-2458.
12. Pathak, V. K. & Temin, H. M. (1990) *Proc Natl Acad Sci USA* 87, 6019-6023.
13. Vartanian, J. P., Meyerhans, A., Asjo, B. & Wain-Hobson, S. (1991) *J Virol* 65, 1779-1788.
14. Suspene, R., Guetard, D., Henry, M., Sommer, P., Wain-Hobson, S. & Vartanian, J. P. (2005) *Proc Natl Acad Sci USA* 102, 8321-8326.
15. Mahieux, R., Suspene, R., Delebecque, F., Henry, M., Schwartz, O., Wain-Hobson, S. & Vartanian, J. P. (2005) *J Gen Virol* 86, 2489-2494.
16. Schmid, A., Spielhofer, P., Cattaneo, R., Baczko, K., ter Meulen, V. & Billeter, M. A. (1992) *Virology* 188, 910-915.
17. Valente, L. & Nishikura, K. (2005) *Prog Nucleic Acid Res Mol Biol* 79, 299-338.
18. Cattaneo, R., Schmid, A., Eschle, D., Baczko, K., ter Meulen, V. & Billeter, M. A. (1988) *Cell* 55, 255-265.
19. Bass, B. L., Weintraub, H., Cattaneo, R. & Billeter, M. A. (1989) *Cell* 56, 331.
20. Samuel, C. E. (2001) *Clin Microbiol Rev* 14, 778-809.
21. O'Hara, P. J., Nichol, S. T., Horodyski, F. M. & Holland, J. J. (1984) *Cell* 36, 915-924.
22. Rueda, P., Garcia-Barreno, B. & Melero, J. A. (1994) *Virology* 198, 653-662.
23. Chang, J., Gudima, S. O. & Taylor, J. M. (2005) *J Virol* 79, 13310-13316.
24. Toth, A. M., Zhang, P., Das, S., George, C. X. & Samuel, C. E. (2006) *Prog Nucleic Acid Res Mol Biol* 81, 369-434.
25. Gommers-Ampt, J. H. & Borst, P. (1995) *Faseb J* 9, 1034-1042.
26. Kirnos, M. D., Khudyakov, I. Y., Alexandrushkina, N. I. & Vanyushin, B. F. (1977) *Nature* 270, 369-370.
27. Bailly, C. & Waring, M. J. (1995) *Nucleic Acids Res* 23, 885-892.
28. Spee, J. H., de Vos, W. M. & Kuipers, O. P. (1993) *Nucleic Acids Res* 21, 777-778.
29. Billecocq, A., Spiegel, M., Vialat, P., Kohl, A., Weber, F., Bouloy, M. & Haller, O. (2004) *J Virol* 78, 9798-9806.
30. Schrag, S. J., Rota, P. A. & Bellini, W. J. (1999) *J Virol* 73, 51-54.
31. Biebricher, C. K. & Eigen, M. (2005) *Virus Res* 107, 117-127.

32. Levanon, E. Y., Hallegger, M., Kinar, Y., Shemesh, R., Djinovic-Carugo, K., Rechavi, G., Jantsch, M. F. & Eisenberg, E. (2005) *Nucleic Acids Res* 33, 1162-1168.
33. Athanasiadis, A., Rich, A. & Maas, S. (2004) *PLoS Biol* 2, e391.
34. Abu-Daya, A. & Fox, K. R. (1997). Interaction of minor groove binding ligands with long AT tracts. Nucleic Acids Res 25, 4962-4969.
35. Abu-Daya, A., Brown, P. M. & Fox, K. R. (1995). DNA sequence preferences of several AT-selective minor groove binding ligands. Nucleic Acids Res 23, 3385-3392.
36. Balanant, J., Guillot, S., Candrea, A., Delpeyroux, F. & Crainic, R. (1991). The natural genomic variability of poliovirus analyzed by a restriction fragment length polymorphism assay. Virology 184, 645-654.
37. Bishop, K. N., Holmes, R. K., Sheehy, A. M., Davidson, N. O., Cho, S.-J. & Malim, M. H. (2004). Cytidine deamination of retroviral DNA by diverse APOBEC proteins. Curr Biol 14, 1392-1396.
38. Goodenow, M., Huet, T., Saurin, W., Kwok, S., Sninsky, J. & Wain-Hobson, S. (1989). HIV-1 isolates are rapidly evolving quasispecies: evidence for viral mixtures and preferred nucleotide substitutions. J Acquir Immune Defic Syndr 2, 344-352.
39. Guillot, S., Caro, V., Cuervo, N., Korotkova, E., Combiescu, M., Persu, A., Aubert-Combiescu, A., Delpeyroux, F. & Crainic, R. (2000). Natural genetic exchanges between vaccine and wild poliovirus strains in humans. J Virol 74, 8434-8443.
40. Janini, M., Rogers, M., Birx, D. R. & McCutchan, F. E. (2001). Human immunodeficiency virus type 1 DNA sequences genetically damaged by hypermutation are often abundant in patient peripheral blood mononuclear cells and may be generated during near-simultaneous infection and activation of CD4+ T cells. J Virol 75, 7973-7986.
41. Jarmuz, A., Chester, A., Bayliss, J., Gisbourne, J., Dunham, I., Scott, J. & Navaratnam, N. (2002). An anthropoid-specific locus of orphan C to U RNA-editing enzymes on chromosome 22. Genomics 79, 285-296.
42. Krawczak, M., Smith-Sorensen, B., Schmidtke, J., Kakkar, V. V., Cooper, D. N. & Hovig, E. (1995). Somatic spectrum of cancer-associated single basepair substitutions in the TP53 gene is determined mainly by endogenous mechanisms of mutation and by selection. *Hum Mutat* 5, 48-57.
43. Li, W. H., Wu, C. I. & Luo, C. C. (1984). Nonrandomness of point mutation as reflected in nucleotide substitutions in pseudogenes and its evolutionary implications. *J Mol Evol* 21, 58-71.
44. Liddament, M. T., Brown, W. L., Schumacher, A. J. & Harris, R. S. (2004). APOBEC3F properties and hypermutation preferences indicate activity against HIV-1 in vivo. Curr Biol 14, 1385-1391.
45. Martinez, M. A., Vartanian, J.-P. & Wain-Hobson, S. (1994). Hypermutagenesis of RNA using human immunodeficiency virus type 1 reverse transcriptase and biased dNTP concentrations. Proc Natl Acad Sci USA 91, 11787-11791.
46. Masny, A. & Ptucienniczak, A. (2003). Ligation mediated PCR performed at low denaturation temperatures—PCR melting profiles. Nucleic Acids Res 31, e114.
47. Muraoka, M., Miles, H. T., Howard, F. B. (1980). Copolymers of adenylic and 2-aminoadenyiic acids. Effect of progressive changes in hydrogen bonding and stacking on interaction with poly(uridylic acid). *Biochemistry* 19, 2429-2439.
48. Sheehy, A. M., Gaddis, N. C. & Malim, M. H. (2003). The antiretroviral enzyme APOBEC3G is degraded by the proteasome in response to HIV-1 Vif. Nat Med 9, 1404-1407.
49. Smith, S. M., Markham, R. B. & Jeang, K. T. (1996). Conditional reduction of human immunodeficiency virus type 1 replication by a gain-of-herpes simplex virus 1 thymidine kinase function. Proc Natl Acad Sci USA 93, 7955-7960.
50. Teng, B., Burant, C. F. & Davidson, N. O. (1993). Molecular cloning of an apolipoprotein B messenger RNA editing protein. Science 260, 1816-1819.
51. Votavova, H., Kucerova, D., Felsberg, J. & Sponar, J. (1986). Changes in conformation, stability and condensation of DNA by univalent and divalent cations in methanol-water mixtures. *J Biomol Struct Dyn* 4, 477-489.
52. Yu, X., Yu, Y., Liu, B., Luo, K., Kong, W., Mao, P. & Yu, X.-F. (2003). Induction of APOBEC3G ubiquitination and degradation by an HIV-1 Vif-Cul5-SCF complex. Science 302, 1056-1060.
53. Yu, Q., Konig, R., Pillai, S., Chiles, K., Kearney, M., Palmer, S., Richman, D., Coffin, J. M. & Landau, N. R. (2004). Single-strand specificity of APOBEC3G accounts for minus-strand deamination of the HIV genome. Nat Struct Mol Biol 11, 435-442.
54. Zheng, Y.-H., Irwin, D., Kurosu, T., Tokunaga, K., Sata, T. & Peterlin, B. M. (2004). Human APOBEC3F is another host factor that blocks human immunodeficiency virus type 1 replication. J Virol 78, 6073-6076.

What is claimed is:

1. A method for the differential amplification of a nucleic acid by polymerization chain reaction (PCR), wherein the method consists essentially of:
   (a) providing a nucleic acid mixture comprising a parental DNA and a GC allele of the parental DNA;
   (b) carrying out PCR in the nucleic acid mixture in a reaction medium containing deoxyinosine (dITP), or in a reaction medium containing deoxy 2,6-diaminopurine triphosphate (dDTP), or in a reaction medium containing dITP and dDTP, wherein Guanine bases (G) are converted into Inosine bases (I) and Adenosine bases (A) are converted into 2,6-diaminopurine bases (D); and
   (c) subjecting nucleic acids of (b) to PCR using a denaturation temperature 1-10° C. lower than the lowest denaturation temperature (Tp) that allows amplification of the parental DNA to thereby selectively amplify the GC allele in the nucleic acid mixture.

2. The method as claimed in claim 1, wherein the denaturation temperature is 1-6° C. lower than the lowest Tp that allows amplification of the parental nucleic acid.

3. The method as claimed in claim 1, wherein the denaturation temperature is 1-3° C. lower than the lowest Tp that allows amplification of the parental nucleic acid.

4. The method as claimed in claim 1, which further comprises detection of one or more of the nucleic acid products of (c).

5. The method as claimed in claim 1, wherein differential amplification is carried out using about equimolar ratio of dTTP, dCTP, dDTP, and dITP.

6. The method as claimed in claim 1, wherein amplifications are carried out with a thermostable DNA polymerase consisting of Taq polymerase.

7. The method as claimed in claim 1, wherein the mixture of nucleic acids is devoid of said parental DNA corresponding to the GC alleleic DNA to be amplified.

8. The method as claimed in claim 1, wherein standard amplification is carried out in the following buffer conditions 2.5 mM $MgCl_2$, 50 mM KCl, 10 mM Tris-HCl (pH 8.3), 200 µM of each primer and 5U of Taq DNA polymerase or a variant thereof in a final volume of 50 µl.

9. The method as claimed in claim 1, wherein the differential amplification is carried out in PCR conditions enabling temperature gradients to be generated in denaturation temperature, in order to enable amplification of the GC alleleic DNA selectively with respect to amplification of the corresponding parental nucleic acid.

10. The method as claimed in claim 9, wherein the temperature gradient for differential amplification is suitable to determine the minimum denaturation temperature for the parental nucleic acid.

11. The method as claimed in claim 1, wherein the differential amplification is carried out in a denaturation temperature gradient in the range of 1 to 15° C.

12. The method as claimed in claim 1, wherein the differential amplification is carried out in a denaturation temperature gradient in the range of 1 to 10° C.

13. The method as claimed in claim 1, wherein the primers used for PCR in differential amplification are devoid of A and T nucleobases in the 1 to 6 nucleotides of their 3' end.

14. The method as claimed in claim 1, wherein the GC alleleic nucleic acid to be enriched is originating from a pathogenic organism or from a gene associated with a pathogenic condition in a host.

15. The method as claimed in claim 14, wherein the pathogenic organism is a DNA virus or a RNA virus.

16. The method as claimed in claim 15, wherein the virus is HIV, MV, or a RVFV.

17. The method as claimed in claim 14, wherein the gene associated with a pathogenic condition in a host relates to a tumor state.

18. The method as claimed in claim 1, wherein the CG alleleic nucleic acid is a A→G, a A→C, a T→G or a T→C allele, variant or mutant of the parental nucleic acid, which pairs with a fully complementary nucleic acid sequence.

19. The method as claimed in claim 1, wherein the CG alleleic nucleic acid variant is a small deletion mutant of the parental nucleic acid.

20. The method as claimed in claim 19, wherein the deletion comprises 1 or 2 bp.

21. The method as claimed in claim 1, wherein the products of the PCR are detected by gel filtration or ion-exchange chromatography.

22. The method as claimed in claim 1, wherein products of the PCR are identified by relative location in the gel.

23. The method as claimed in claim 1, wherein the modified bases are dITP or dDTP.

24. The method as claimed in claim 1, wherein step b) of amplification of nucleic acids by PCR is carried out with non-standard PCR buffer comprising tetraethyl-ammonium chloride, methanol, or polyethylene glycol.

25. The method as claimed in claim 1, wherein the parental nucleic acid comprises 40 to 500 bases.

26. The method as claimed in claim 1, wherein the parental nucleic acid comprises 40 to 80 bases.

27. The method as claimed in claim 1, wherein the window of observation is between 10-30 bases.

28. A method of differential DNA denaturation PCR (3DI-PCR), wherein the method consists essentially of:
   (a) providing a nucleic acid mixture comprising a parental DNA having up to about 500 bp and a GC allele of the parental DNA having up to about 500 bp;

(b) carrying out PCR in the nucleic acid mixture in a reaction medium containing deoxyinosine (dITP), deoxy 2,6-diaminopurine triphosphate (dDTP), or dITP and dDTP, wherein Guanine bases (G) are converted into Inosine bases (I) and Adenosine bases (A) are converted into 2,6-diaminopurine bases (D); and (c) subjecting nucleic acids of (b) to PCR using primers having about 20-25 bp at a denaturation temperature 1-10° C. lower than the lowest denaturation temperature (Tp) that allows amplification of the parental nucleic acid, to thereby selectively amplify a region of about 20-80 bp of the GC allele of the parent DNA in the nucleic acid mixture.

29. The method as claimed in claim 28, wherein the denaturation temperature is 1-6° C. lower than the lowest Tp that allows amplification of the parental nucleic acid.

30. The method as claimed in claim 28, wherein the denaturation temperature is 1-3° C. lower than the lowest Tp that allows amplification of the parental nucleic acid.

31. The method as claimed in claim 28, which further comprises detection of one or more of the nucleic acid products of (c).

32. The method as claimed in claim 28, wherein differential amplification is carried out using about equimolar ratio of dTTP, dCTP, dDTP, and dITP.

33. The method as claimed in claim 28, wherein the differential amplification is carried out in PCR conditions enabling temperature gradients to be generated in denaturation temperature, in order to enable amplification of the GC alleleic nucleic acid selectively with respect to amplification of the corresponding parental nucleic acid.

34. The method as claimed in claim 28, wherein the differential amplification is carried out in a denaturation temperature gradient in the range of 1 to 15° C.

35. The method as claimed in claim 28, wherein the differential amplification is carried out in a denaturation temperature gradient in the range of 1 to 10° C.

36. The method as claimed in claim 28, wherein the primers used for PCR in differential amplification are devoid of A and T nucleobases in the 1 to 6 nucleotides of their 3 end.

37. The method as claimed in claim 28, wherein the products of the PCR are detected by gel filtration or ion-exchange chromatography.

38. The method as claimed in claim 28, wherein products of the PCR are identified by relative location in the gel.

39. The method as claimed in claim 28, wherein the modified bases are dITP or dDTP.

40. A method of inverse differential DNA denaturation PCR (3DI-PCR), wherein the method consists essentially of:

(a) providing a nucleic acid mixture comprising a parental DNA and a mutant DNA of the parental DNA containing 2-5 GC alleleic sites;

(b) carrying out PCR in the nucleic acid mixture in a reaction medium containing deoxyinosine (dITP), deoxy 2,6-diaminopurine triphosphate (dDTP), or dITP and dDTP, wherein Guanine bases (G) are converted into Inosine bases (I) and Adenosine bases (A) are converted into 2,6-diaminopurine bases (D); and (c) subjecting nucleic acids of (b) to PCR using primers having about 20-25 bp at a denaturation temperature 1-10° C. lower than the lowest denaturation temperature (Tp) that allows amplification of the parental nucleic acid, to thereby produce a differentially amplified PCR fragment of 60-80 bp of the GC allele of the parent nucleic acid in the nucleic acid mixture.

41. The method as claimed in claim 40, wherein the denaturation temperature is 1-6° C. lower than the lowest Tp that allows amplification of the parental nucleic acid.

42. The method as claimed in claim 40, wherein the denaturation temperature is 1-3° C. lower than the lowest Tp that allows amplification of the parental nucleic acid.

43. The method as claimed in claim 40, which further comprises detection of one or more of the nucleic acid products of (c).

44. The method as claimed in claim 40, wherein differential amplification is carried out using about equimolar ratio of dTTP, dCTP, dDTP, and dITP.

45. The method as claimed in claim 40, wherein the products of the PCR are detected by gel filtration or ion-exchange chromatography.

46. The method as claimed in claim 40, wherein the differential amplification is carried out in PCR conditions enabling temperature gradients to be generated in denaturation temperature, in order to enable amplification of the GC-rich mutant nucleic acid selectively with respect to amplification of the corresponding parental nucleic acid.

47. The method as claimed in claim 46, wherein the differential amplification is carried out in a denaturation temperature gradient in the range of 1 to 15° C.

48. The method as claimed in claim 47, wherein the differential amplification is carried out in a denaturation temperature gradient in the range of 1 to 10° C.

49. The method as claimed in claim 40, wherein the primers used for PCR in differential amplification are devoid of A and T nucleobases in the 1 to 6 nucleotides of their 3' end.

50. The method as claimed in claim 40, wherein the denaturation temperature is 1-3° C. lower than the lowest Tp that allows amplification of the parental nucleic acid, differential amplification is carried out using about equimolar ratio of dTTP, dCTP, dDTP, and dITP, and differential amplification is carried out in a denaturation temperature gradient in the range of 1 to 10° C., and the primers used for PCR in differential amplification are devoid of A and T nucleobases in the 1 to 6 nucleotides of their 3' end.

51. The method as claimed in claim 50, which further comprises detection of one or more of the nucleic acid products of (c).

52. The method as claimed in claim 50, wherein the mutant nucleic acid in (a) contains 3 or 4 GC alleleic sites.

53. The method as claimed in claim 50, wherein the mutant nucleic acid in (a) contains two GC alleleic sites.

54. The method as claimed in claim 52, wherein the denaturation temperature gradient is 63° C. to 72° C.

55. The method as claimed in claim 54, wherein the mutant DNA contains about 2 alleleic sites per 265 bp.

* * * * *